US006447777B1

(12) United States Patent
Terman et al.

(10) Patent No.: US 6,447,777 B1
(45) Date of Patent: Sep. 10, 2002

(54) POLYMERIZED STAPHYLOCOCCAL PROTEIN A FOR TREATMENT OF DISEASES

(75) Inventors: David Stephen Terman, Pebble Beach, CA (US); Raoul F. Reiser, Sarasota, FL (US)

(73) Assignee: David S. Terman, Pebble Beach, CA (US)

( * ) Notice: Subject to any disclaimer, the term of this patent is extended or adjusted under 35 U.S.C. 154(b) by 0 days.

(21) Appl. No.: 08/828,951

(22) Filed: Mar. 28, 1997

Related U.S. Application Data

(60) Provisional application No. 60/024,802, filed on Mar. 29, 1996.

(51) Int. Cl.[7] ........................ A61K 39/02; A61K 38/00; C07K 1/00; A60K 39/085

(52) U.S. Cl. ................................ 424/184.1; 424/237.1; 424/236.1; 424/243.1; 424/280.1; 530/350; 530/387.1; 514/12; 514/18

(58) Field of Search .............................. 530/350, 387.1, 530/868; 424/184.1, 237.1, 236.1, 243.1, 280.1; 514/12, 18

(56) References Cited

U.S. PATENT DOCUMENTS

| | | | | |
|---|---|---|---|---|
| 4,223,672 | A | * | 9/1980 | Terman et al. |
| 4,699,783 | A | | 10/1987 | Terman et al. |
| 4,957,738 | A | * | 9/1990 | Patarroyo |
| 4,996,194 | A | * | 2/1991 | Cohen et al. |
| 5,091,091 | A | * | 2/1992 | Terman et al. |
| 5,149,794 | A | * | 9/1992 | Yatvin et al. |
| 5,256,641 | A | * | 10/1993 | Yatvin et al. |
| 5,370,871 | A | * | 12/1994 | Dintzis et al. |
| 5,519,114 | A | * | 5/1996 | Johnson et al. |
| 5,693,326 | A | * | 12/1997 | Lees |
| 5,707,624 | A | * | 1/1998 | Nickoloff et al. |
| 5,728,388 | A | * | 3/1998 | Terman |
| 5,756,449 | A | * | 5/1998 | Andersen et al. |
| 5,783,214 | A | * | 7/1998 | Royer |

FOREIGN PATENT DOCUMENTS

| | | | |
|---|---|---|---|
| EP | 432629 | * | 6/1991 |
| EP | 544115 | * | 6/1993 |
| WO | 9736614 | * | 10/1997 |

OTHER PUBLICATIONS

Rose et al Immunology Today 14/9:426–430, 1993.*
Terman, J. Biol. Response Modifers 3:316–324, 1984.*
Heijnen et al. J. Clin. Invest. 97(2):331–338, Jan. 1996.*
Gesselin et al, J. Immunol. 149(11):3477–3481, 1992.*
Fuleihan et al. J. Immunol. 146(5):1661–1666, 1991.*
Terman, Methods In Enzymology 137:496–515, 1988.*
Balint et al, Cancer Research, 44: 737–743, 1984.*
Ezepchuk et al, J. Invest. Dermatol. 107:603–609, 1996.*
Terman et al, Eur. J. Cancer. Clin. Oncol. 21/10:1115–1122, 1985.*
Blackman et al, Life Sciences, 57/19:1717–1735, 1995.*
Daskal et al, Cancer Research 44:2225–2235, 1984.*
Ihle et al, Cancer Research. 55:623–628, 1995.*
Langone et al, J. Immunol. 133/2: 1057–1063, 1984.*
Miller et al, Applied & Environmental Microbiol 36/3:421–426, 1978.*
Gidlöf et al, Eur. J. Haematol, 60:233–239, 1998.*
Gidlöf et al. Blood, 89/6:2089–2097, 1997.*
Snyder, H.W. et al, Seminars in Hematology (1989) 26, No. 2, pp. 31–41.
Terman, D.S., Crit. Revs. Oncology/Hematology 4:2, pp. 103–125 (1985).

* cited by examiner

*Primary Examiner*—Nita Minnifield
(74) *Attorney, Agent, or Firm*—Scott R Bortner

(57) ABSTRACT

Polymers and polymer conjugates comprising crosslinked Staphylococcal protein A, or crosslinked protein A-superantigen, or crosslinked functional derivatives thereof ranging in size from 12kDa to 1O,OOOkDa are useful in the treatment of autoimmune diseases, such as rheumatoid arthritis and ITP as well as neoplastic diseases. Compositions and pharmaceutical composition comprising chemically crosslinked polymers of protein A alone or protein A and bacterial enterotoxins, optionally further complexed with immunoglobulins and complement components, are disclosed, as are methods for making and using these compositions in the treatment of diseases. Plasma perfusates of protein A immunadsorbent columns in clinical use are shown to act through the leaching of polymers of protein A and protein A-Staphylococcal enterotoxin B having a broad range of molecular masses. Methods of treating patients by monitoring column plasma perfusates for either of these chemical entities and appropriately adjusting doses of perfusate are also disclosed.

29 Claims, 9 Drawing Sheets

POLYMERIZED STAPHYLOCOCCAL PROTEIN A FOR TREATMENT OF DISEASES

This application claims benefit of provisional application Ser. No. 60/024,802 filed Mar. 29, 1996.

BACKGROUND OF THE INVENTION

1. Field of the Invention

This invention in the fields of biochemistry and medicine is concerned with chemically crosslinked Staphylococcal protein A, Staphylococcal enterotoxins or functional derivatives thereof and their use alone or in combination with immunoglobulins or complement components in the treatment of autoimmune and neoplastic diseases.

2. Description of the Background Art

Protein A is a constituent of the cell wall of many strains of bacteria of the species *Staphylococcus aureus*. This protein (abbreviated "SpA" herein) has molecular weight of 42 kDa and binds selectively to immunoglobulins (Igs), particularly IgG, and immune complexes from many mammalian species. Ig binding sites for SpA are located in the Fc region of the Ig molecule. SpA-Ig complexes display diverse biological activities including complement binding and activation (Langone, J. J., Adv. Immunol. 32:157–252 (1982)).

An immunoadsorbent column consisting of SpA immobilized on collodion-coated charcoal was originally used for ex vivo immunoadsorption and provided successful extracorporeal treatment for patients with breast carcinoma (Terman, D. S., U.S.Pat. No. 5,091,091, Feb. 2, 1995). Subsequently, a SpA-silica immunoadsorbent column was developed by Bensinger, Kinet and others (Bensinger, U.S. Pat. No. 4,614,513., Sep. 30, 1986; Bensinger W. I. et al., *New Eng. J Med* 306:935 (1982); Kinet, J. P. et al., *Eur. J Clin Invest.* 16:50–55 (1986)) and later by Balint et al.(U.S. Pat. No. 4,681,870, Jul. 21, 1987). This column, known by its trade name of Prosorba®, produced by IMRE Corporation, has received FDA approval for treatment of idiopathic thrombocytopenic purpura (ITP) and hemolytic-uremic syndrome. Prosorba® columns have also been reported to show efficacy against advanced cancer and autoimmune diseases such as rheumatoid arthritis (RA) (Balint et al., supra; Snyder, H. W. et al., *J Clin. Apheresis* 7:110:118 (1992); Snyder, H. W. et al., *Sem. Hematol* 26:31 (1989); Mittelman, A. et al., *Sem. Hematol.* 26:15 (1989); Messerschmidt, G. L. et al., *Sem. Hematol.* 26:19 (1989); Snyder, H. W. et al, *J Clin. Apheresis* 6:1 (1991); Snyder, H. W. et al., *Blood* 79:2237 (1992)). Clinically, these columns may be used in an "on-line" or "off-line" mode with identical therapeutic effects. In the off-line mode, 200 ml of plasma is collected by phlebotomy from a subject, passed over the column and then returned to the same donor. Publications sponsored by the manufacturer of the column (IMRE Corporation) indicate that the coupling of SpA to silica creates a "stable covalent bond" such that the bound SpA is not released into the perfused plasma (Snyder, H. W. et al., *J Clin. Apheresis* 7:110:118 (1992); Snyder, H. W. et al., *Sem. HematoL* 26:31 (1989); Mittelman, A. et al., *Sem. Hematol.* 26:15 (1989); Messerschmidt, G. L. et al, *Sem. Hematol.* 26:19(1989); Snyder, H. W. et al., *J Clin. Apheresis* 6:1 (1991). Snyder, H. W. et al., *Blood* 79:2237 (1992); Balint, J. P., *Blood* 84:664 (1994)). The removal of immune complexes from plasma perfused over the column is said to be the basis of the column's therapeutic effect. However, despite the purported covalent bonding of the SpA to the column matrix, several investigators (including the manufacturer) have reported that SpA does indeed leach from the column surface into the perfused plasma in amounts that have been reported to vary from 200 $\mu$g to 1 mg of SpA per treatment dose of perfused plasma (Sato, H. et al., *Transfusion Sci.* 12:299 (1991); Kinet, J. P. et al., *Eur. J Clin. Invest.* 16:43 (1986); *IMRE Corporation FDA Safety and Efficacy Report on Prosorba® Column,* 1987).

The clinical toxicity of the procedure (Smith, E. et al., *J Clin. Apheresis* 7:4 (1992); Ciavarella, D. et al., *Int. J Clin. Lab. Res.* 21:210 (1992); Dzic, W., *New Eng. J Med* 331:792 (1994)) and the known in vivo and in vitro biological effects of SpA (Langone, J. J., *J Biol. Resp. Modif.* 3:241 (1984)) might have hinted that leached SpA was of biotherapeutic significance. Nevertheless, according to the present state of the art, there is no pharmacologic significance ascribed to the leached material. Rather, the art teaches that the therapeutic effects of these columns are due entirely to the adsorption and removal by the column of immune complexes from plasma (supra). Accordingly, there has been no attempt, prior to the work leading up to the present invention, to examine carefully the composition of products leaching from these columns or to characterize their molecular structure and biologic activity.

IMRE Corporation scientists have demonstrated antitumor effects in human cancer patients (overall response rate of 30%) using the Prosorba® column. The best responses were seen in patients with breast cancer and Kaposi's sarcoma (Messerschmidt, G. L. et al., *J Clin. Oncol.* 6:203-212 (1988)). The authors ascribed the effect to adsorption of circulating immune complexes from tumor bearing plasma to the Prosorba® column. However, as viewed by the present inventor in light of the invention disclosed herein, it is more likely that the effects were due to complexes of (1) leached SpA and IgG, (2) leached SpA and Staphylococcal enterotoxin B (SEB) and/or (3) SpA, SEB and IgG. The variability of patient responses is likely due to the unpredictability and the broad range of the amount of leached polymeric or complexed SpA emerging from the column.

B. Anergy or Sensitization Induced by SpA-SEB-IgG Complexes

Enterotoxins are known to produce T cell anergy or sensitization depending on the dose (Sundstedt, A. et al., *J Immunol.* 154:6306–6313 (1995)). For example, very large or very small doses of enterotoxins produce anergy whereas intermediate doses produce sensitization. As noted above, the effectiveness of Prosorba® in the treatment of an autoimmune disease (ITP, RA) and cancer was thought to be due to the adsorption and removal of immune complexes by the column.

Based on the present invention, the contention that the therapeutic effects of Prosorba® (in ITP, for example) are due to "immune complex removal" from 200 ml of plasma by the column would seem far-fetched. According to such reasoning, the mere removal of this volume of plasma by phlebotomy (the first step of Prosorba® treatment) should show the same or greater therapeutic efficacy since withdrawing 200 ml of blood effectively, by definition, removes 100% of the immune complexes contained therein. However, neither phlebotomy alone nor plasmapheresis effects any change in the clinical course of ITP or other diseases in which Prosorba® has been effective. A comparative study of the therapeutic effects of the two treatments in ITP further corroborates this assertion (Kiprov, D. D. et al., *J Clin. Apheresis* 3:133 (1986)).

The present inventor is the first to have found that the basis for therapeutic activity of the Prosorba® column in ITP and RA is not what it is claimed to be. Rather, by analyzing what elutes from these columns under various conditions, including conditions of standard clinical use, the present inventor has discovered novel compositions which represent significant, totally unexpected improvements in the treatment of autoimmune diseases such as ITP and RA and of cancer. In making this invention, the present inventor has characterized this eluted material and has designed novel therapeutic compositions and methods for treating autoimmune and neoplastic diseases.

SUMMARY OF THE INVENTION

The present inventor has identified SpA in perfusates of SpA immunoadsorbent columns and has shown that it originates from material associated with the column which is not covalently bound to the column matrix. The fundamental discovery for the present invention, was that plasma emerging from the SpA column contained SpA that could be in a monomeric form or in a polymerized, crosslinked high molecular weight form. In fact, SpA which desorbs from the column using various forms of mild perfusion is predominantly in the form of SpA oligomers or polymers. These discoveries were made using a SpA immunoadsorbent column prepared in the laboratory under conditions similar to those specified by the IMRE Corporation and approved by the FDA for clinical use.

When administered to patients with autoimmune disease or cancer, such leached monomeric SpA or SpA polymers readily combine with IgG in host plasma to form high molecular weight SpA-IgG complexes. The therapeutic effects of the SpA polymers of the present invention in ITP patients are believed to be due to the prior complexing of the SpA polymers with IgG. These complexes, mimicking immune complexes, bind to FcR of macrophages, lymphocytes and platelets (Dima, S. et al., *Eur. J. Immunol.* 13:605 (1983); Kinet, J. P. et al., In: *Human Neoplasms, in Selective Plasma Component Removal*, A. Pineda, ed., pp. 105 (1984); Sulica, A. et al., *Immunology* 38:173 (1979); Hawiger, J. et al., *J Clin. Invest.* 64:931 (1979); Kay, H. S. et al., *J Immunol.* 118:2058 (1977); Dosset, J. H. et al., *J Immunol.* 103:1405 (1969); Austin, R. M. et al., *J Immunol.* 117:602 (1976); Forgsgren, A. et al., *J Immunol.* 112:1177 (1974)). Indeed, complexes made up of polymeric SpA and IgG are far more effective than previously described monomeric SpA-IgG complexes in blocking FcR-associated functions (Terman, D. S. et al., U.S. Pat. No. 4,699,783, Oct. 13, 1987). Hence, these polymers are extremely efficient in FcR blocking and can achieve the pharmacologic effects at relatively low doses, thereby minimizing the systemic toxicity associated with administration of larger amounts of SpA (which may be due to the SpA itself or to contaminating molecules such as enterotoxins).

Based on the observations of the present inventor disclosed herein, the clinical effects of Prosorba® may be related in part to the amount of SEB complexed with and accompanying the leached SpA polymers. Ratios of SpA to enterotoxin B of about 1000 (by weight) will produce antitumor effects. In contrast, ratios >1000, with SEB in quantities >1 ng/ml of column perfusate, by inactivating T cells may not result in antitumor effects. Leached SEB in intermediate amounts, between 1 ng/ml and 1 μg/ml may result in T cell desensitization and anergy.

Indeed, according to the present invention, the therapeutic effect of Prosorba® in autoimmune diseases is due in part to the induction of (1) T cell anergy by leached enterotoxins and (2) B cell tolerance by high molecular weight crosslinked SpA polymers. The effects of Prosorba® in cancer is due to systemic delivery of sensitizing doses of enterotoxins present in the polymerized SpA complexes. B cells are known to express Fcγ receptors with affinity for SpA. Although monomeric SpA is a potent B cell mitogen, high polymerized covalently crosslinked SpA is thought to induce B cell anergy, even in small quantities.

According to the present invention, organic chemical methods, preferably carbodimide crosslinking are used to produce crosslinked SpA molecules. These chemically crosslinked "oligomers or polymers" are then employed therapeutically, preferably (a) by direct intravenous injection or (b) by prior complexing with IgG, with specific antibodies (preferably the IgG isotype) or with complement components followed by administration to a subject. Hence, this invention permits the achievement of the positive clinical effects of SpA column "immunoadsorption" procedures without the need for the expensive columns, the manpower and technical expertise required to carry out the column preparation and perfusion procedures, the unpredictable quantity of leached products, and the toxic side effects accompanying the column-based therapy. By prescribing the amount and form of SpA to be infused to a patient, the present invention avoids the toxicity while improving the therapeutic index of the agent.

Specifically, the present invention is directed to a therapeutic composition useful for treating an autoimmune or neoplastic disease comprising a mixture of monomeric and crosslinked polymeric SpA molecules or a functional derivative of a SpA molecule, wherein (a) the cross-linked polymer molecule comprises at least two monomeric units of SpA or of the functional derivative; and (b) at least 10% of the total protein or functional derivative is in the form of polymers In the above composition, the crosslinked SpA or functional derivative molecules preferably comprise polymers having a range of molecular masses from about 12 kDa to about 10,000 kDa.

In another embodiment of the above composition, the average molecular mass of the polymers is at least 500 kDa and at least about 50% of the total SpA or functional derivative is in the form of polymers. In yet another embodiment, the average molecular mass of the polymers is between about 64 kDa and about 1000 kDa; and at least about 70% of the total SpA or functional derivative is in the form of polymers. Alternatively, the average molecular mass of the polymers is between about 64 kDa and about 10,000 kDa; and at least about 90% of the total SpA or functional derivative is in the form of polymers.

The present invention also provides the above composition wherein the polymeric SpA or functional derivative is complexed with immunoglobulin (Ig) molecules to form a polymeric SpA-Ig complex. Other useful a therapeutic compositions comprise the polymeric SpA-Ig complexes further complexed with complement components to form a SpA-Ig-complement complex. The Ig is preferably IgG. The IgG may be a purified specific antibody, including a mAb.

The present invention is directed to a polymeric SpA composition wherein the SpA or functional derivative is further crosslinked with molecules of a bacterial superantigen or a functional derivative thereof to form a mixture of (a) polymeric crosslinked SpA or SpA functional derivative, (b) polymeric crosslinked conjugates of i. SpA-superantigen, ii. SpA functional derivative-superantigen, iii. SpA-superantigen functional derivative, or iv. SpA functional derivative-superantigen functional derivative; and (c) polymeric crosslinked superantigen or superantigen functional derivative. The bacterial superantigen is preferably selected from a group consisting of an enterotoxin of Staphylococcus aureus, toxic shock syndrome toxin, a Streptococcus pyrogenic exotoxin, a *Mycoplasma arthritides* toxin and a *Yersinia enterocolitica* toxin.

Also provided is a composition useful for treating an autoimmune or neoplastic disease comprising a chemically crosslinked polymer of SpA, or of a functional derivative of SpA, and having the following characteristics: (a) immunoglobulin Fc binding activity is less than half that of native SpA; and (b) immunoglobulin $V_H3$ region binding is more than about twice that of native SpA. The SpA polymer may be further crosslinked to molecules of a bacterial superantigen or functional derivative thereof The present invention is further directed to a method for preparing a therapeutic compositions as described above, which comprises treating SpA or the functional derivative with a crosslinking agent under conditions which result in crosslinking of the SpA or the functional derivative or both to produce the composition.

A preferred embodiment of the method comprises treating a mixture of SpA and a bacterial superantigen with a crosslinking agent under conditions which results in crosslinking of any one of (a) SpA or its functional derivative with like molecules; (b) SpA with superantigen; (c) SpA functional derivative with superantigen; (d) SpA with superantigen functional derivative; (e) SpA functional derivative with superantigen functional derivative; or (f) superantigen or its functional derivative with like molecules.

Another embodiment provides a method for reducing the toxicity of monomeric enterotoxin molecules, comprising mixing the enterotoxin molecules with SpA or an SpA functional derivative, adding a crosslinking agent capable of crosslinking the enterotoxin molecules and the SpA and allowing any enterotoxin to be chemically crosslinked with the SpA, thereby reducing the toxicity. Alternatively, toxicity can reduced by simply crosslinking enterotoxin molecules with themselves.

In the foregoing methods, the crosslinking agent is selected from the group consisting of a carbodiimide, a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative and a homobifunctional photoreactive compound.

The above crosslinking agent is preferably a carbodiimide selected from the group consisting of 1-cyclohexyl-3-(2-morpholinyl-(4-ethyl) carbodiimide, (1-ethyl-3-(3-dimethyaminopropyl carbodiimide (EDC) and 1-ethyl-3-(4-azonia-4,4-dimethylpentyl) carbodiimide.

The crosslinking agent may also be a heterobifunctional compound selected from the group consisting of compounds having:

(a) an amine-reactive and a sulfhydryl-reactive group;

(b) an amine-reactive and a photoreactive group; and (c) a carbonyl-reactive and a sulfhydryl-reactive group.

In the crosslinking method may be performed by coupling a carbonyl group to an amine group or to a hydrazide group by reductive amination.

Also provided is a method for preparing a therapeutic composition comprising cross-linking the mixture of SpA or the functional derivative and the superantigen, as described above, with a carrier, which carrier consists of a protein, lipid or other polymer which can be covalently bonded to the SpA or the derivative and the superantigen, thereby creating a heterogeneous polymer complex. When the carrier is a protein it is preferably serum albumin, keyhole limpet hemocyanin, tetanus toxoid, ovalbumin, thyroglobulin, diphtheria toxoid, myoglobin, immunoglobulin or purified protein derivative of tuberculin. The carrier may be polymer selected from the group consisting of a polysaccharide, a poly(amino acid), a poly(vinylalcohol), a polyvinylpyrrolidone, a poly(acrylic acid), a polyurethane and a polyphosphazene.

In one embodiment of the above method, the crosslinking produces a SpA polymer or SpA-superantigen polymer covalently bonded to a liposome.

In the foregoing methods, the bacterial superantigen is preferably an enterotoxin of *Staphylococcus aureus*, toxic shock syndrome toxin, a Streptococcus pyrogenic exotoxin, a *Mycoplasma arthritides* toxin or a *Yersinia enterocolitica* toxin.

In the above method for preparing a therapeutic composition comprising a complex between polymeric SpA or a functional derivative thereof and Ig, the method preferably comprises incubating a composition as described above with a fluid containing Ig and allowing the formation of the complex. The fluid is preferably plasma and the Ig is preferably IgG. In one embodiment, the fluid preferably contains a specific antibody of the IgG isotype.

The present invention provides a method for preparing a therapeutic composition useful to for treating an autoimmune or neoplastic disease which composition comprises a complex between polymeric SpA or a functional derivative thereof, Ig and complement, the method comprising (a) incubating a mixture of monomeric and crosslinked polymeric SpA molecules or a functional derivative of a SpA molecule, as above, with a fluid containing Ig, preferably IgG, to produce a mixture containing Ig bound to the polymeric SpA or functional derivative;

(b) adding to the mixture of step (a) complement or components thereof and allowing the formation of the complex.

The invention is also directed to a pharmaceutical composition useful for treating a subject with an autoimmune or neoplastic disease, comprising (a) an effective amount of a composition as described above; and (b) a pharmaceutically acceptable excipient or carrier. The composition may further be bonded to or sequestered within a liposome vesicle.

Also provided herein is a method of treating a subject with an autoimmune disease or cancer, comprising administering to the subject the above pharmaceutical composition.

In a method of extracorporeal treatment of a subject having an autoimmune or neoplastic disease, wherein, over a course of one or more treatments, plasma of the subject is perfused through a SpA-silica immunoadsorbent column to produce a perfusate, and the perfusate is reinfused to the subject, the present invention provides an improvement which comprises:

(a) over the course of one or more treatments, perfusing plasma of the subject through the column;

(b) at each treatment, measuring the amount of SpA in the perfusate prior to the reinfusing;

(c) when the amount of total SpA in the perfusate is less than about 2 μg, increasing the volume of the perfusate or increasing the number of doses of the perfusate such that the subject receives between about 2 μg and about 200 μg per treatment;

(d) when the amount of total SpA in the perfusate is greater than about 200 μg, decreasing the volume of the perfusate such that the subject receives between about 2 μg and about 200 μg per treatment; thereby treating the subject. In another embodiment of the above extracorporeal treatment method, the improvement comprises:

(a) over the course of one or more treatments, perfusing plasma of the subject through the column;

(b) at each treatment, measuring the amount of bacterial enterotoxins in the perfusate prior to reinfusing;

(c) when the amount of total bacterial enterotoxins in the perfusate is less than about 1 ng, increasing the volume of the perfusate or increasing the number of doses of the perfusate such that said subject receives between about 1 ng and about 200 ng per treatment;

(d) when the amount of total bacterial enterotoxins in the perfusate is greater than about 200 ng, decreasing the volume of said perfusate such that the subject receives between about 1 ng and about 200 ng per treatment, thereby treating the subject.

DESCRIPTION OF THE PREFERRED EMBODIMENTS

Figure 1:
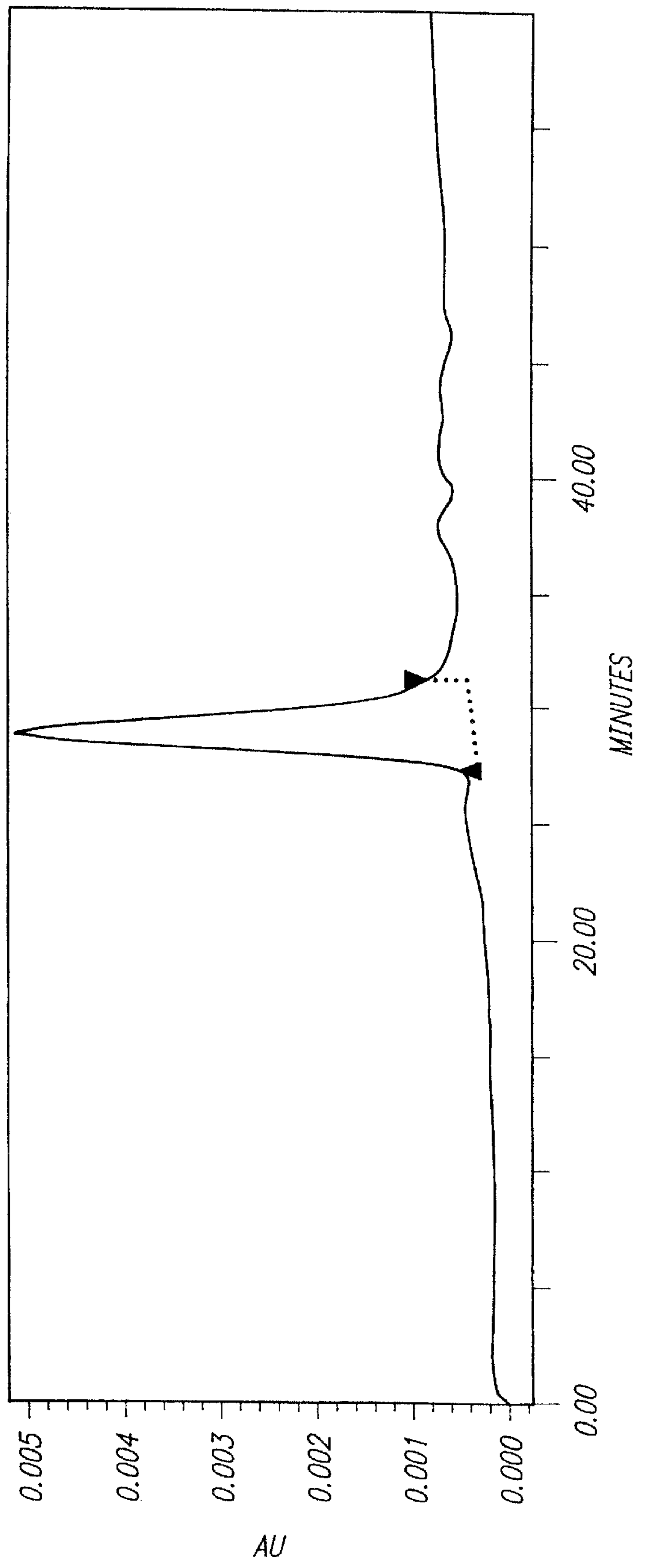
FIG. 1 is a chromatogram resulting from gel filtration chromatography of recombinant SpA on a Superose 6 FPLC column. SpA was dissolved in water at a concentration of 0.2 mg/ml and 200TI of this solution was injected on the column. The buffer used for the chromatography was 0.02M sodium phosphate, 0.15M NaCl, pH7.2. The elution was monitored by absorbance at 280nm.

The present invention provides a composition comprising SpA polymers or oligomers useful for treating a subject with an autoimmune or a neoplastic disease. Autoimmune (or other immune-related diseases) which may be treated include but are not limited to ITP, RA, systemic lupus erythematosus, multiple sclerosis, transplant rejection, paraneoplastic syndrome, hemolytic anemia. A more complete, though not exhaustive, list of autoimmune diseases treatable by the present invention appears in Tables 1–2. Neoplasms treatable by this invention include carcinomas of breast, lung, colon, kidney, melanomas, lymphomas and leukemias. Infectious diseases include AIDs and HIV related diseases.

TABLE 1

| DISEASES WITH AN AUTOIMMUNE ETIOLOGY OR COMPONENT | |
|---|---|
| HEUMATIC DISEASES: | HEMATOLOGIC DISEASES: |
| Rheumatoid Arthritis | Hypersplenism |
| Juvenile Rheumatoid Arthritis | Systemic Lupus Erythematosus |
| Systemic Lupus Erythematosus (SLE) | Felty's Syndrome |
| Sjögren's Syndrome' | Autoimmune Neutropenia |

TABLE 1-continued

| DISEASES WITH AN AUTOIMMUNE ETIOLOGY OR COMPONENT | |
|---|---|
| Progressive Systemic Sclerosis | Immune Hemolytic Anemias |
| Polymyositis-Dermatomyositis | Idiopathic Thrombocytopenic Purpura (ITP) |
| Behcet's Disease | Secondary Autoimmune |
| Ankylosing Spondylitis | Thrombocytopenia |
| Reiter's Syndrome | Neonatal Thrombocytopenias |
| Psoriatic Arthritis | Autoimmune |
| Polychondritis | Maternal |
| Panniculitis | Autoimmune Myocarditis |
| Hereditary Complement Disease | EYE DISEASES: |
| Hypogammaglobulinemia and Arthritis | Vernal Conjunctivitis |
| NEUROLOGIC DISEASES: | Atopic Keratoconjunctivitis |
| Acute Disseminated Encephalomyelitis | RESPIRATORY DISEASES: |
| Multiple Sclerosis (MS) | Goodpasture's Syndrome |
| Guillain-Barre Syndrome | Idiopathic Pulmonary Fibrosis |
| Myasthenia Gravis | Sarcoidosis |
| Myasthenic (Eaton-Lambert) Syndrome | RENAL DISEASES: |
| Paraneoplastic Cerebellar Degeneration | Anti-Glomerular Basement Membrane |
| Amyotrophic Lateral Sclerosis | Antibody-Induced Glomerulonephritis |
| Alzheimer's disease | Immune-Complex Glomerulonephritis |
| Multiple Myeloma | Tubulointerstitial Nephritis |
| Waldenström's Macroglobulinemia | DERMATOLOGIC DISEASES: |
| Primary Systemic Amyloidosis | Bullous Pemphigoid |
| ENDOCRINE DISEASES: | Herpes Gestationis |
| Hashimoto's Disease (Chronic Thyroiditis) | Dermatitis Herpetiformis |
| Transient Thyroiditis Syndromes | Epidermolysis Bullosa Acquisita |
| Grave's Disease | Pemphigus Vulgaris |
| Primary Hypothyroidism | Pemphigus Foliaceus |
| Type I Diabetes Mellitus | Discoid Lupus Erythematosus |
| Addison's Disease | |
| Lymphocytic Adenohyophysitis | |
| Idiopathic Hypoparathyroidism | |
| Autoimmune Polyglandular Syndromes Types I–III | |
| Premature Ovarian Failure | |

TABLE 2*

DISORDERS ASSOCIATED WITH AUTOIMMUNE DEFECTS

| Disorder | Mechanism or Evidence |
|---|---|
| I. Autoimmune Disorders | |
| Hashimoto's Thyroiditis | Cell-mediated and Humoral Thyroid Cytotoxicity |
| Systemic Lupus Erythematosus (SLE) (SLE) | Circulating and Locally Produced Immune Complexes |
| Goodpasture's Syndrome | Anti-Basement Membrane Antibodies |
| Pemphigus | Epidermal Acantholytic Antibody |
| Graves' Disease | Thyroid Stimulating Hormone Receptor Antibody |
| Myasthenia Gravis | Acetylcholine Receptor Antibody |
| Insulin Resistance | Insulin Receptor Antibody |
| Autoimmune Hemolytic Anemia | Phagocytosis of Antibody-Sensitized Red Cells |
| ITP | Phagocytosis of Antibody-Sensitized Platelets |
| Rheumatoid Arthritis | Immune Complexes in Joints |
| Scleroderma (Anti-Collagen Antibodies) | Nucleolar and other Nuclear Antibodies |
| Mixed Connective Tissue Disease | Antibody to Extractable Nuclear Antigen (ribonucleoprotein) |
| Polymyositis | Nonhistone Anti-Nuclear Antibody |
| Pernicious Anemia | Antiparietal Cell, Microsomes, and Intrinsic Factor Antibodies |
| Idiopathic Addison's Disease | Humoral and Cell-Mediated Cytotoxicity |
| Infertility (some) | Antispermatozoal Antibodies |
| Glomerulonephritis | Glomerular Basement Membrane Antibody or Immune Complexes |
| Bullous Pemphigoid | IgG and Complement in Basement Membrane |
| Sjögren's Syndrome | Multiple Tissue Antibodies; Specific Nonhistone |

TABLE 2*-continued

DISORDERS ASSOCIATED WITH AUTOIMMUNE DEFECTS

| Disorder | Mechanism or Evidence |
|---|---|
| | Antinuclear Antibody (SS-B) |
| Diabetes Mellitus (some) | Cell-mediated Reaction and Islet Cell Antibodies |
| Adrenergic Drug Resistance (with asthma and cystic fibrosis) | β-Adrenergic Receptor Antibody |
| Candidate Autoimmune Diseases | |
| Chronic Active Hepatitis | Smooth Muscle Antibody |
| Primary Biliary Cirrhosis | Mitochondrial Antibody |
| Other Endocrine Gland Failure | Specific Tissue Antibodies (some) |
| Vitiligo | Melanocytic Antibody |
| Vasculitis | IgG and Complement in Vessel Walls; Low Serum Complement (some) |
| Post-Myocardial Infarction, Cardiotomy Syndrome | Myocardial Antibody |
| Urticaria, Atopic Dermatitis, Asthma (some) | IgG and IgM Antibodies to IgE |
| Numerous Other Inflammatory, Granulomatous, Degenerative and Atrophic Disorders | No Reasonable Alternative Explanation |

*See Merck Manual, p. 340

The term "polymer" or "oligomer" used interchangeably herein refers to a molecular entity comprising of two or more monomeric units of a protein or a peptide fragment thereof The monomers are preferably covalently bonded, most preferably crosslinked. The terms "polymer" and "crosslinked polymer" are intended to encompass polymers which are bonded "end to end." It is understood that such crosslinked polymers or oligomers may include additional atoms not native to the protein or peptide and which are derived from the crosslinking agent.

A "polymer" or "oligomer" comprising SpA generally refers to a homopolymer, that is, an entity consisting of monomeric units of an SpA protein or peptide fragment thereof In one embodiment, a polymer includes monomers which are non-identical SpA peptide fragments produced by crosslinking a mixture of intact SpA proteins and/or various peptide fragments thereof Other preferred polymers or oligomers of the present invention include crosslinked bacterial enterotoxin molecules, preferably Staphylococcal enterotoxin B (SEB). Included within the scope of this invention are other Staphylococcal enterotoxins such as enterotoxin A (SEA), enterotoxin C (SEC), and the like.

When unlike proteins or peptides are combined in a preparation, this is termed a "polymeric conjugate" or "heteropolymer." An example is a polymer or oligomer made by crosslinking SpA protein and/or peptide fragments thereof with other proteins homologous to SpA from other bacterial species, or with peptide fragments thereof Polymers and polymer conjugates may also comprise other Staphylococcal immunoglobulin binding proteins (IBP) that function in accordance with the present invention. Examples include Staphylococcal protein G (SpG) or a recombinant fusion protein between SpA and protein G ("SpA/G"). Protein G of Group G and Group C streptococci binds to the Fc portion of Ig molecules as well as to IgG Fab fragment at the $V_H3$ domain. Protein C of *Peptococcus magnus* binds to the Fab region as well. Any other microbial IBP proteins, for example from Streptococci, are also intended (see, for example, Langone, J. J., *Adv. Immunol.* 32:157 (1982)).

A preferred polymeric conjugate comprises crosslinked SpA and SEB or SpA and another related bacterial enterotoxin, as described above. Such polymeric conjugates may also include peptide fragments of the full length bacterial proteins. Other bacterial toxins or "superantigens" intended within the scope of this invention are discussed below.

In the polymers of the present invention, the monomeric units of each protein or peptide are preferably randomly linked, such that any given polymeric structure (whether a polymer or a polymer conjugate) may contain a variable number and variable structural arrangement of monomers. However, the total amount of SpA in the final composition is preferably in the ranges delineated herein.

The polymers may be produced by recombinant means, for example in the form of fusion proteins or as products of sequentially arranged genes that encode a protein having more than one unit of SpA (or a fragment or derivative thereof) or one or more units of SpA and one or more units consisting of all or a fragment of another protein such as a bacterial superantigen. Hence, polymers as well as polymer conjugates made by recombinant methods (rather than by chemical means) are included herein.

Also provided herein are complexes between the polymers or polymeric conjugates above and: (1) immunoglobulin (Ig) molecules, preferably IgG (2) purified specific antibodies of any isotype to which SpA binds or which have a variable region domain to which SpA binds, or (3) complement (C') components. The complexing can be through Fc region binding sites on the Ig, or alternatively, via Ig $V_H3$ region binding sites. These complexes are preferably produced by incubating the polymer or polymeric conjugate with an appropriate concentration of an Ig or of a specific antibody (affinity-purified polyclonal or monoclonal) to yield a high molecular weight polymeric SpA-Ig complex. It is understood that SpA may also bind IgG, IgM or IgA in their Fab region, specifically in the $V_H3$ domain. These Igs may include IgM rheumatoid factors (Silverman, G. et al., *Int. Rev. Immunol.* 9:57 (1992)). In another embodiment, the polymeric SpA-Ig complex is incubated with a source of C' proteins, such as fresh serum, to allow C' components to bind to the SpA-IgG complex and yield a polymeric SpA-Ig-C' complex. In another embodiment, the above incubation with Ig or C' is performed in the presence of a crosslinking agent (described below) to generate covalently crosslinked SpA-Ig or SpA-Ig-C' complexes.

As stated above, this invention is based on the discovery that a composition comprising polymerized SpA as well as polymeric conjugates of SpA and SEB are the active agents, both therapeutic and toxic, when a subject's plasma is perfused through a SpA immunoadsorbent column and reinfused into the subject. Thus, in one aspect, this discovery provides the basis for monitoring SpA immunoadsorbent columns for therapeutic efficacy and safety and provides the rationale for the direct chemical approach to modifying SpA (as disclosed herein) and administration of this new composition as a better characterized and more active (and thus more economical) agent for therapy of these diseases. When monitoring such columns, the amount of SpA and/or SEB (or other Staphylococcal enterotoxins) in the plasma perfusate is measured by conventional means prior to reinfusion into the subject. The volume of plasma perfusate is adjusted up or down from that used conventionally so that it delivers to the subject a dose (per single treatment) of between about 0.1 $\mu$g and 1000 $\mu$g SpA, more preferably between about 2$\mu$g and 200 $\mu$g SpA, or between about 0.01ng and 1000 ng SEB, more preferably between about 1 ng and 200 ng SEB.

A therapeutic amount of the novel SpA composition is effective to treat an autoimmune, neoplastic or infectious disease, as described in detail below. The desired therapeutic amount may also be measured in an in vitro test for example by measuring the level of complement consumption and generation of anaphylatoxin when the SpA polymer is added to fresh plasma. Other in vitro assays are described below.

A method of treating a patient having autoimmune, neoplastic or infectious disease is also provided. The method comprises parenteral administration of a composition according to this invention to a subject patient in need of such treatment. The composition may be a polymeric SpA, a polymeric conjugate of SpA and an enterotoxin or a complex of either of the above with Ig (preferably IgG) or Ig and C'. The composition may consist of SpA bound to Ig molecule in their Fc portion, where it is generally known to bind. Alternatively, the SpA may be bound to the Ig molecules at a biding site in the $V_H3$ domain of the Ig heavy chain, particularly in IgM or IgA, or at any other binding sites in the Fab region of the Ig molecule.

APPLICATION TO HIV AND HIV RELATED DISORDERS

An additional preferred embodiment is based on the use of the superantigenic domain of protein A to block the binding of gp 120, the HIV envelope antigen, to CD4+ cells where it contributes to the apoptotic process. A high proportion of CD4+ T cells from HIV-1-infected individuals are abnormally primed in vivo to undergo cell death by apoptosis upon mobilization of their T cell receptor for antigen (TCR). The mechanisms by which T cells from HIV-infected patients undergo AICD involve two steps. First, there is a priming step in a region with a high burden of infection where many CD4+T cells circulate, leading to interactions between uninfected T cells and viral envelope antigen gp120 and/or HIV infected APCs. Secondly, there is a restimulation phase which occurs when T cells recirculate in the periphery at which time CD4+ cells undergo apoptosis. The gp 120 molecule also binds to B cells via the $V_H3$ region on the IgG recptor and programs these cells for apoptosis.

The superantigenic receptor on protein A for $V_H3$ regions of immunoglobulins is known to reside in the domain D region of the molecule. This domain may be readily expressed and cloned after transfection of the gene for native or mutant domain D into an E. coli. Procedures to accomplish this are well described in the art. A protein A molecule capable of binding only to $V_H3$ may be prepeared by blocking the Fc receptor binding by treatment of the molecule with iodine monocholoride. Thus domain D or chemically modified protein A which bind to $V_H3$ may be administered parenterally. These molecules are capable of competitively interfering with binding of the HIV protein gp 120 to the $V_H3$ region on B cells or CD4receptors on T 15 cells. Once bound, the HIV envelope antigen is capable of inducing apoptosis in CD4+T cell especially when these cells receive a second signal via the TCR as with a mitogen. Hence, domain D or chemically modified protein A may be used in HIV disorders to prevent gp 120 induced programming of B and T cells for apoptosis.

The protein A region D fragments may be given parenterally with relative safety. Upon entering the circulation domain D will compete with the gp120 protein for binding to $V_H3$ on B cells and CD4 on CD4+ cells and therefore prevent gp120 from preprogramming B and T cells for apoptosis after a second signal. The modified protein A or domain D of protein A may be administered bi-weekly. Dosages may vary from 1 ug/kg to 500 ug/kg depending on the gp120 load in the circulation. Higher loads of gp120 will require doses of domain D or modified protein A to neutralize and/or bind the envelope antigen. In vitro testing of quantitative binding would be predictive of the amount of protein A or domain D that would be required in order to eliminate all of the circulating pool of gp120 antigen.

In a preferred embodiment, the therapeutic composition is administered intravenously. The composition can be administered once, but is preferably administered six to twelve times at intervals which may range from daily administration to administration biweekly or at intervals of about one week to four weeks. Repeating the full treatment regimen is also contemplated, as described hereinafter.

A more detailed description of the components of the therapeutic composition, followed by a description of the treatment method, is provided below.

PROTEIN A

A preferred therapeutic composition comprises a SpA polymer preparation. For effective therapy, the amount of total SpA present in a therapeutic composition of this invention is between about 1 and 1000 $\mu$g per treatment, or between about 0.01 and 20 $\mu$g/kg body weight. Preferably, the amount of SpA in a unit dose is about 20 $\mu$g. The purity of the SpA component should be assured, preferably by producing it using recombinant methods. These methods are well-known in the art and are not set forth in detail herein. Recombinant SpA is commercially available (e.g., from Repligen (Cambridge, Mass.). Purification of SpA is well known in the art (Sjoquist, J. et al., *E. J Biochem.* 29:572 (1972); Balint, J., *J Immunol. Meth.* 116:37 (1989)).

The monomeric SpA should show a single band corresponding to a molecular mass of 42 kDa on polyacrylamide gel electrophoresis (PAGE) under reducing conditions. The SpA should produce a sharp peak with minimal shouldering on high performance liquid chromatography (HPLC).

SpA produced by a method other than recombinant technology, for example by purification from a biological source, preferably has a level of purity similar to recombinant SpA. The SpA composition of the present invention is preferably substantially free from other substances with which it is natively associated, e.g. endotoxins, nucleases and proteases. Excluded, of course, from this list are those substances which are described herein as being desirable in polymer conjugates with SpA for the present compositions and methods (e.g., enterotoxins).

ENTEROTOXINS

In a preferred embodiment, one or more bacterially derived superantigens, preferably enterotoxins, are present in the therapeutic composition. These are either produced recombinantly, by chemical synthesis or purified from native sources, using methods known in the art. See, for example, Ranelli, D. M. et al., *Proc. Natl. Acad. Sci. USA* 82:850–854 (1985); Iandolo, J. J. *Annu. Rev. Microbiol.* 43:375 (1989); Kappler, J. W. et al., *J Exp. Med* 175:387 (1992); Rahim, A. et al., *J Exp. Med.* 180:615 (1994; Lando, P. A. et al., *Canc. Immunol. Immunother.* 33:231 (1991) Dohlsten, M. et al., 88:9287 (1991); Dohlsten, M. et al., Immunology 79:520 (1993); Dohlsten, M. *Proc. Natl. Acad. Sci.* USA (1994); Marrack, P. et al., Science 248:750 (1990); and Terman, D. S. et al., PCT Publication W091/10680 (1991).

Most preferred superantigens are *Staphylococcus aureus* enterotoxins A, B, C 1, C2, D or E (SEA, SEB, SEC 1, SEC2, SED, SEE). Examples of other preferred enterotoxins or superantigens are: *Streptococcus pyogenes* toxins A and C (SPE-A and SPE-C; *Staphylococcus aureus* toxic shock syndrome-associated toxin (TSST-1); *Staphylococcus aureus* exfoliating toxins A and B (ETA and ETB) and Staphylococcus aureus alpha toxin.. Also included are toxins from *Mycoplasma arthritides* and *Yersinia enterocolitica*. Various enterotoxins share differing degrees of immunological relatedness (Bergdoll, M. S. et al., *Infect. Immun.* 4: 593 (1971); Bergdoll, M. S., Enterotoxins. In: *STAPHYLOCOCCIAND STAPHYLOCOCCI INFECTIONS*, C. S. F. Easmon et al., eds, pp. 559–598, 1983, London, Academic Press; Freer, J. H. et, *J Pharmacol. Pharm. Ther.* 19:55 (1983). Immunologic cross-reactivity between SPE-A, SEB and SEC 1 suggests the presence of a conserved domain. SEA, SEB, SEC, SED, TSST-1 and the pyrogenic exotoxins share considerable DNA and amino acid sequence homology. The enterotoxins, the pyrogenic exotoxins and TSST-1 therefore appear to be evolutionarily related and all belong to a common generic group of proteins. SPE-A and SPE-C are about as similar to each of the Staphylococcal toxins as they are to each other. Exfoliative toxins have sizes similar to SEB and SEA and similar modes of action. They share several regions of sequence similarity to the Staphylococcal enterotoxins. Overall there are several stretches of protein having similarities throughout the total group of Staphylococcal enterotoxins, Streptococcal pyrogenic exotoxins and Staphylococcal exfoliative toxins. The structural homologies between the enterotoxins and the *S. pyogenes*, toxins, above, apparently are responsible for the identity of clinical responses to them. These toxins induce hypotension, fever, chills and septic shock in humans, apparently by inducing cytokines such as interleukin- 1, interleukin-2, tumor necrosis factors, interferons and procoagulant activity which are the prime mediators of the clinical symptoms. Additional agents which are candidates for use in accordance with this invention in place of an enterotoxin, based upon structural homology or identity of clinical effects, are gram positive bacterial products, cell wall bacterial constituents such as peptidoglycans and various gram negative bacterial components including products of Meningococci, Pseudomonas and *E. coli.*

An effective dose of an enterotoxin in the therapeutic methods of this invention is between about 0.001ng and 5ng per treatment or between about 0.01 and 100 pg/kg body weight per treatment. The purity of the enterotoxin may be assured by producing it using recombinant methods although enterotoxins isolated by biochemical means are also included. In its monomeric form, an enterotoxin preferably shows a single band corresponding to a molecular mass of 28 kDa on PAGE (under reducing conditions) and a sharp peak on HPLC. The enterotoxin component of the present composition should be substantially free of other substances with which it is natively associated, e.g., endotoxins, nucleases and proteases, but not necessarily free of SpA or its homologues or analogues.

SPECIFIC ANTIBODIES

In another embodiment a purified specific antibody (Ab), either purified from a polyclonal antiserum or a monoclonal Ag (mAb), is crosslinked with SpA or peptides thereof to form polymeric conjugates of SpA-Ab. Such a composition is particularly useful for targeting FcR-bearing cells to target cells bearing the specific antigen to which the Ab is directed (e.g., tumor cells).

SpA COMPLEXED WITH $V_H3$ PORTION OF IMMUNOGLOBULIN

As stated above, SpA has a binding site in the $V_H3$ domain of the Ig heavy chain in addition to its better known binding to Fc. Because radioiodination of SpA by the chloramine-T method, which attacks tyrosine residues, is known to diminish its ability to bind to the Ig Fc region, it would be expected that crosslinking SpA via tyrosine residues would produce a similar effect. It is further expected SpA crosslinked in this manner will bind selectively to the $V_H3$ region of Ig molecules. Thus, use of any crosslinking agent which (a) crosslinks at tyrosine, (b) directly or allosterically inactivates the Fc binding sites of SpA, will selectively produce SpA polymers (or SpA-superantigen polymer conjugates) which are “targeted” to the $V_H3$ domain of Ig. Carbodiimides, in particular EDC achieve this effect. Such crosslinked SpA polymers are useful for any purpose in which it is desirable to bind Ig at $V_H3$. For example, such $V_H3$-targeted SpA polymers interact with B lymphocyte surface IgM molecules and can modulate activation of these cells, for example, inhibiting the production of rheumatoid factor by B cells in the joints or tissues of RA patients. Hence, one mechanism by which the present compositions are effective in treating RA, or other autoimmune diseases in which B cell activation must be controlled, is via direct action on B cells to cause anergy or apoptosis. Alternatively, SpA polymer-Ig complexes (with or without crosslinked superantigen) wherein the Ig is bound at the $V_H3$ domain, will also bind to FcR-bearing cells, such as synoviocytes and fibroblasts in RA, and downregulate their activation, secretion of cytokines and release of degradative enzymes. Hence, in a preferred embodiment, this invention provides an SpA polymer or SpA-superantigen polymer conjugate wherein the SpA is crosslinked at tyrosine residues or at other residues which result in inactivation of binding to Ig Fc sites and enhanced binding to Ig $V_H3$ sites. Also provided are methods for producing such polymers and methods of using such polymers to treat autoimmune diseases, particularly RA.

B cell tolerance, anergy or apoptosis may be induced by SPA-IgG complexes over a broad ratio of IgG to SpA. This effect is conditioned by the stage of B cell maturation, the efficiency of complex presentation and its binding affinity. SpA-IgG complexes are capable of crosslinking surface Fc receptors or the Fcγ (FcγRII) receptor with the antigen or immunolobulin receptor on B cells to provide an inhibitory signal perhaps by closing the plasma membrane calcium channels. For B cells, there is a very narrow dosage stimulation range for such complexes and a very large dosage range for induction of anergy. Cell types to include but not limited to actively proliferating or secreting B cells such as autoantibody or rheumatoid factor producing B cells or gp120 stimulated B cells are susceptible to anergy induction. Binding of the IgG $V_H3$ sites on B cell IgG-receptors by some protein A-IgG complexes may lead to deletion or apoptosis. T and B cell activation by this process with associated IL-2 production may augment the process of B cell apoptosis.

Fibroblasts present in rheumatoid synovium contribute to the local T cell mediated inflammation in rheumatoid joints by exerting an anti-apoptotic effect on T cells. Indeed, apoptosis in synovial T cells may be inhibited by fibroblasts present in rheumatoid synovium by secretion of cytokines including, but not limited to, IL- 15. Fibroblast secretory and phagocytic function may be paralyzed after binding of SpA-IgG complexes to Fc receptor rendering these cells incapable of exerting antiapoptotic effects on synovial T cells.

SpA dissociates from the protein A column after both saline and plasma perfusion. A portion of the saline wash is pooled with perfused plasma before infusion into patients. Hence, the solution administered to patients contains a mixture of desorbed protein A generated from both plasma and saline perfusion. The SpA generated from the column after perfusion with saline is predominantly in monomeric form and that generated from plasma perfusion is mainly in polymeric form. Both forms of SpA will combine with IgG in plasma to form SpA-IgG complexes. It should be recognized that although the major form of protein A infused into patients after protein A perfusion is as high molecular weight polymers, there is also some monomeric protein A released which is infused as well. Thus, the protein A infused is a heterogeneous population of monomers and polymers. Although most of the protein A combines with IgG in plasma, some may be present in native form as monomers or polymers. Monomeric protein A combined with IgG forms complexes with an empiric formula of $IgG_4$ $SpA_2$. Polymers of SpA and IgG may have a broad spectrum of ratios. Finally, the protein A -IgG complexes are quite dynamic once exposed to plasma readily exchanging with free IgG to form complexes with varying IgG content.

Some of the protein A-IgG complexes include enterotoxins which bind to surface class II receptors on B cells and Vβ receptors on T cells. B cell anergy results from the direct effect of the enterotoxins on B cell class II or $V_H4$ receptors or indirectly via T cell activation by enterotoxins crosslinking B cells to the T cell TCR. B cell anergy results from interleukin release by activated T cells or direct T cell contact with B cells. Indeed, enterotoxins such as SED bind to $V_H4$ region of surface immunoglobulins on B cells and also bind T cell TCR. SpA-IgG-enterotoxin complexes induce anergy or apoptosis in B cells by binding to B cell class II receptors via the enterotoxin and to Fc and IgG sites by means of the SPA-IgG component while crosslinking the B cell to the T cell TCR via the enterotoxin moiety. Preprogrammed B or T cells with bound antigen or gp120 are susceptible to apoptosis when confronted with a second mitogenic or activating signal in the form of SpA-IgG-enterotoxin complexes. Local release of IL-2 by activated B or T cells during the process will further promote cell death.

Protein A-IgG complexes of various sizes have different biologic functions once they are administered in the host. Large complexes may will block reticuloendothelial cell function by binding to Fc receptors on fibroblasts, endothelial cells or macrophages. After binding to fibroblasts they inhibit cytokine release and exert anti-apoptotic effects on synovial T cells. SpA-IgG complexes also bind to B cell Fc and IgG receptors to induce anergy or apoptosis. SPA-IgG-enterotoxin complexes will crosslink B cells to the TCR of T cells via class II receptors on B cells and induce anergy or apoptosis in both T and B cells. Cell types to include but not limited to actively proliferating T cells and IgG secreting B cells including rheumatoid factor and autoantibody producing B cells are most susceptible to apoptosis induction following these stimuli.

In summary, the SPA-IgG-enterotoxin complexes released from the protein A columns after plasma perfusion are diverse in size and display multiple therapeutic functions such as inactivating B cells and synovial fibroblasts, paralyzing reticuloendothelial function by binding to macrophages and anergizing T and B cells via enterotoxin crosslinking. B cell driven isotype immunoglobulin switching may also be inhibited by SPA-IgG-enterotoxin mediated bridging of T and B cells. Some of the larger complexes may deposit on the surface of macrophages or synoviocytes or fibroblasts to produce antiphagocytic and anti-apoptotic effects on synovial T cells while smaller conjugates will bind to B cell Fc and IgG receptors to induce anergy and/or apoptosis.

FUNCTIONAL DERIVATIVES OF SpA or SUPERANTIGEN PROTEIN OR PEPTIDE

The term SpA or polymeric SpA is intended to encompass functional derivatives of SpA or of an SpA peptide. Similarly, Staphylococcal enterotoxins or superantigens are intended to encompass functional derivatives of a particular superantigen or enterotoxin.

By "functional derivative" is meant a "fragment," "variant," "homologue," "analogue,"or "chemical derivative" of SpA or of an enterotoxin, which terms are defined below. A functional derivative retains at least a portion of the function of the native protein monomer which permits its utility in accordance with the present invention.

A "fragment" refers to any shorter peptide. A "variant" of refers to a molecule substantially similar to either the entire protein or a peptide fragment thereof. Variant peptides may be conveniently prepared by direct chemical synthesis of the variant peptide, using methods well-known in the art.

SpA fragments are known in the art (see Langone, J. J., *Adv. Immunol.* 32:157–252 (1982) for review) and are preferred functional derivatives for use in accordance with the present invention. Six tryptic fragments of SpA were originally identified as overlapping sequences (designated I–VI). Two of these, originally termed A and B by Hjelm et al. (*Europ. J Biochem.* 57:395–403 (1975)) had MWs between 6 and 7kDa and each bound Fc monovalently. Domains designated A, B, C and D were later obtained as fragments (Sjodahl. J., *Eur. J Biochem.* 73:343–351 (1977); Sjodahl, J. *Eur. J. Biochem.* 78:471–479 (1977)). These fragments comprise 58, 58, 59 and 61 amino acids, respectively and have MWs of about 6kDa. These fragments are consecutively arranged from the N-terminal part of SpA in the order D, A, B and C. This N-terminal 27kDa of SpA contains all the Fc-binding activity of the protein. The known sequences of these four domains shows that they are mutually homologous and also contain internal homologies. Each of these fragments binds to the $C_H2$ and $C_H3$ domains of Fc. Hence, crosslinked polymers and polymers conjugates which include one or more of these four defined fragments of SpA are useful for treating diseases as discussed for SpA. The smallest polymer comprising two monomers of one (or more) of these fragments would have a MW of about 12kDa. A monovalent fragment of SpA ("fSpA") with a MW of 13kDa modulates effector functions of IgG, such as complement fixation, catabolism, binding to FcRs and antibody-dependent cellular cytotoxicity (ADCC) (Ghetie, V. et al., *Mol. Immunol.* 23:377–384 (1986)). An fSpA-like protein obtained from a particular Staphylococcal strain (A676) is mitogenic to, and enhances NK activity of, human peripheral lymphocytes. Fragment B binds to and alters the Fc site of IgG which controls the catabolism of IgG; this site is in the $C_H2$ domain and differs from the FcR binding site (Dima, S. et al., *Europ. J Immunol.* 13:605–614 (1983)).

A homologue refers to a natural protein, encoded by a DNA molecule from a different species, which shares a minimum amount of structure and thereby function with the reference protein. Homologues, as used herein, typically share about 50% sequence similarity at the DNA level or about 18% sequence similarity in the amino acid sequence.

An "analogue" refers to a non- natural molecule substantially similar to either the entire molecule or a fragment thereof.

A "chemical derivative" contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

The recognition that the biologically active regions of the enterotoxins and SPE-A, for example, are substantially structurally homologous enables predicting the sequence of synthetic peptides which exhibit similar biological effects in accordance with this invention (Johnson, L. P. et al., *Mol. Gen. Genet.* 203:354–356 (1886).

A common method for evaluating sequence homology, and more importantly, for identifying statistically significant similarities, is by Monte Carlo analysis using an algorithm written by Lipman and Pearson to obtain a Z value. According to this analysis, Z>6 indicates probable significance, and Z>10 is considered to be statistically significant (Pearson, W. R. et al., *Proc. Natl. Acad. Sci. USA,* 85:2444–2448 (1988); Lipman, D. J. et al., Science 227:1435–1441 (1985)). In the present invention, synthetic peptides corresponding to SpA on the one hand, or to enterotoxins are the other hand, are characterized in that they are substantially homologous in amino acid sequence to SpA or an enterotoxin with statistically significant (Z>6) sequence homology and similarity to include alignment of cysteine residues and similar hydropathy profiles. 1. Variants One group of variants are those in which at least one amino acid residue in the peptide molecule, and preferably, only one, has been removed and a different residue inserted in its place. For a detailed description of protein chemistry and structure, see Schulz, G. E. et. al., Principles of Protein Structure, Springer-Verlag, New York, 1978, and Creighton, T. E., Proteins: Structure and Molecular Properties, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1–2 of Schulz et al. (supra) and FIGS. 3–9 of Creighton (supra). Based on such an analysis, conservative substitutions are defined herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp. The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Tyr, because of its hydrogen bonding potential, has some kinship with Ser, Thr, etc.

Substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of Gly or Pro; (b) substitution of a hydrophilic residue, e.g., Ser or Thr, for (or by) a hydrophobic residue, e.g., Leu, Ile, Phe, Val or Ala; (c) substitution of a Cys residue for (or by) any other residue; (d) substitution of a residue having an electropositive side chain, e.g., Lys, Arg or His, for (or by) a residue having an electronegative charge, e.g., Glu or Asp; or (e) substitution of a residue having a bulky side chain, e.g., Phe, for (or by) a residue not having such a side chain, e.g., Gly.

Most deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays, for example direct or competitive immunoassay or biological assay as described herein. Modifications of such proteins or peptide properties as redox or thermal stability, hydrophobicity, susceptibility to proteolytic degradation or the tendency to aggregate with carriers or into multimers are assayed by methods well known to the ordinarily skilled artisan.

In the present invention, functional derivatives of enterotoxins or other related toxins include synthetic polypeptides characterized by substantial structural homology to enterotoxin A, enterotoxin B and Streptococcal pyrogenic exotoxins with statistically significant sequence homology and similarity (e.g., Z>6 in the Lipman and Pearson algorithm in Monte Carlo analysis (see above)). 2. Chemical Derivatives Covalent modifications of the monomeric or polymeric forms of SpA or peptide fragments thereof, of enterotoxins or peptide fragments thereof, or both included within the scope of this invention. Such modifications may be introduced into the molecule by reacting targeted amino acid residues of the protein or peptide with an organic derivatizing agent that is capable of reacting with selected side chains or terminal residues. This may be accomplished before or after polymerization.

Cysteinyl residues most commonly are reacted with α-haloacetates (and corresponding amines), such as 2-chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4- nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3- butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides as noted above. Aspartyl and glutamyl residues are converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecule Properties, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences,* 16th ed., Mack Publishing Co., Easton, Pa. (1980).

FORM AND PRODUCTION OF SpA OR OTHER IMMUNOGLOBULIN BINDING PROTEIN

The SpA can be present in the therapeutic composition of the present invention as a polymer, polymeric conjugate, or as a mixture of monomers, polymers and/or polymeric conjugates. In one embodiment, at least 80% of the total weight of the SpA in the composition is present in polymeric form (either homopolymer or polymeric conjugate).

The crosslinked SpA polymeric molecule of the present invention comprises at least two monomeric units of SpA or of a functional derivative of SpA. Preferably, at least 10% of the total mass of SpA or functional derivative is in the form of polymers. When the polymers are polymers of full-length SpA monomers, the SpA polymers preferably have a molecular mass of at least 64kDa. When the polymers are polymers of SpA fragments, then the MW is at least about 12kDa. In another embodiment, the average molecular mass of the SpA polymers in the composition is at least 500kDa, and at least 50% of the total mass of SpA (or functional derivative) is in the form of a polymer. The average molecule mass of the SpA polymer preferably varies from about 64 kDa to about 1000 kDa and even up to about 10,000 kDa. Where the SpA "unit" of the polymer is a fragment or other functional derivative having a MW less than that of a full length SpA protein, then the minimum MW of the present polymer may be less than 64 kDa. The percentage of total SpA or functional derivative in the composition which is in the form of a polymer or polymer conjugate preferably varies from about 10% to 90%. It is to be understood that any amount of polymer present in admixture with monomeric SpA is a novel attribute of the present invention. Hence, the amount of polymer in a mixture may vary up to 100% polymeric SpA.

SpA polymers and polymer conjugates can be formed using conventional crosslinking agents such as carbodiimides as used in preparing the SpA-silica immunoadsorbent columns (Terman, 1995, supra; Bensinger, 1986, supra; Bensinger et al., 1982, supra; Kinet, J. P. et al., 1986, supra; Balint et al., 1987, supra). Examples of carbodiimides are 1-cyclohexyl-3-(2-morpholinyl-(4-ethyl) carbodimide (CMC), 1-ethyl-3-(3-dimethyaminopropyl carbodiimide (EDC) and 1-ethyl-3-(4-azonia-4,4-dimethylpentyl) carbodiimide. Examples of other suitable crosslinking agents are cyanogen bromide, glutaraldehyde and succinic anhydride. In general any of a number of homobifunctional agents including a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative and a homobifunctional photoreactive compound may be used. Also included are heterobifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homobifunctional crosslinking agents include the bifunctional N-hydroxysuccinimide esters dithiobis(succinimidylpropionate), disuccinimidyl suberate, and disuccinimidyl tartarate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio)propion-amido] butane, bismaleimidohexane, and bis-N-maleimido-1,8-octane; the bifunctional aryl halides 1,5-difluoro-2,4-dinitrobenzene and 4.4'-difluoro-3,3'-dinitrophenylsulfone; bifunctional photoreactive agents such as bis-[β-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butanediol diglycidyl ether, the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N,N'-ethylene-bis(iodoacetamide), N,N'-hexamethylene-bis(iodoacetamide), N,N'-undecamethylene-bis(iodoacetamide, as well as benzylhalides and halomustards, such as α, α'-diiodo-p-xylene sulfonic acid and tri(2-chloroethyl)amine, respectively.

Crosslinking may be accomplished by coupling a carbonyl group to an amine group or to a hydrazide group by reductive amination.

Polymers also may be prepared by non-covalent attachment of monomers through ionic, adsorptive, or biospecific interactions. Complexes of SpA with highly positively or negatively charged molecules may be done through salt bridge formation under low ionic strength environments, such as in deionized water. Large complexes can be created using charged polymers such as poly-(L-glutamic acid) or poly-(L-lysine) which contain numerous negative and positive charges, respectively. Adsorption of SpA may be done to surfaces such as microparticle latex beads or to other hydrophobic polymers, forming non-covalently associated SpA, effectively mimicking crosslinked or chemically polymerized protein. Finally, SpA may be non-covalently linked through the use of biospecific interactions between other molecules. For instance, utilization of the strong affinity of biotin for proteins such as avidin or streptavidin or their derivatives could be used to form polymeric SpA species. These biotin-binding proteins contain four binding sites that can interact with biotin in solution or covalently attached to another molecule (Wilchek, M. et al., *Anal. Biochem.* 171:1–32 (1988). SpA can be modified to posses biotin groups using common biotinylation reagents such as the N-hydroxysuccinimidyl ester of D-biotin (NHS-biotin) which reacts with available amine groups on the protein. Biotinylated SpA then can be incubated with avidin or streptavidin to create large complexes. The molecular mass of such polymers can be regulated through careful control of the molar ratio of biotinylated SpA to avidin or streptavidin. The incorporation of biotinylated superantigen molecules to this complex can be done as well.

The therapeutic composition of the present invention may be prepared by crosslinking a mixture of SpA (or functional derivative) and a superantigen (or a functional derivative) with a carrier. The carrier preferably consists of a protein, a lipid or another polymer which can be covalently bonded to SpA (or derivative) and the superantigen. Preferred protein carriers include serum albumin, keyhole limpet hemocyanin, tetanus toxoid, ovalbumin, thyroglobulin, diphtheria toxoid, myoglobin, immunoglobulin and purified protein derivative of tuberculin. A non-protein polymer carrier may be a polysaccharide, a poly(amino acid), a poly(vinyl alcohol), a polyvinylpyrrolidone, a poly(acrylic acid), a polyurethane and a polyphosphazene. The SpA polymer or SpA-superantigen polymer conjugate may be covalently bonded to a liposome.

PHARMACEUTICAL COMPOSITIONS AND THEIR PREPARATION

A pharmaceutical composition according to this invention comprises the novel polymer or polymer conjugate described herein in a formulation that, as such, is known in the art. Thus the compositions may be in the form of a lyophilized particulate material, a sterile or aseptically produced solution, a tablet, an ampule, etc. Vehicles, such as water or other aqueous solutions preferably buffered to a physiologically acceptable pH (as in phosphate buffered saline) or other inert solid or liquid material such as normal saline or various buffers may be present. The particular vehicle is not critical, and those skilled in the art will readily know which vehicle to use for any particular utility described herein.

SpA is highly soluble in aqueous solutions, as are polymers and polymer conjugates thereof. The polymer or polymer conjugate may be maintained in liquid or lyophilized form.

In general terms, a pharmaceutical composition is prepared by mixing, dissolving, binding or otherwise combining the polymer or polymeric conjugate of this invention with one or more water-insoluble or water-soluble aqueous or non-aqueous vehicles. If necessary, another suitable additive or adjuvant is included. It is imperative that the vehicle, carrier or excipient, as well as the conditions for formulating the composition are such that do not adversely affect the biological or pharmaceutical activity of the polymer or polymer conjugate.

The SpA polymers described herein have the following advantages when used in accordance with the present invention:

1. They are more efficient than monomeric SpA at blocking FcRs on FcR-bearing cells.
2. They combine with far more IgG than does monomeric SpA thereby forming larger complexes of SpA-IgG.
3. The larger complexes readily localize to FcR-bearing cells in spleen and liver which are the major effector organs in the case of ITP.
4. Polymerized SpA reduces the toxic action of any crosslinker or accompanying enterotoxin B by sterically hindering its functional and antigenic recognition sites.
5. Polymerized SpA may be conveniently and easily synthesized using chemical crosslinking agents without requiring the construction of the elaborate immobilized SpA silica-silane system.
6. The synthetically polymerized SpA may be readily quantitated, and a measurable and predictable amount may be administered in an appropriate vehicle to a patient.

This constitutes a major advance in the safety and effectiveness of administration of polymerized SpA compared to the use of the SpA column wherein polymerized SpA is generated inadvertently and in unpredictably quantities upon use of the column by perfusing with plasma. An insufficient amount of released SpA in this "accidental" preparation would impair therapeutic effectiveness; an excess would lead to life threatening toxicity.

ADMINISTRATION AND METHODS OF USE OF SpA COMPOSITIONS

Normally the polymer or polymer conjugate will be sold and administered in predispensed unit dosage forms, each one containing an effective amount of the conjugate that is preferably in the range 10 μg–50 mg per unit dose. The exact dosage varies from case to case and depends on patient's weight and age, administration route, type of disease, toxicity and can readily be determined by the skilled artisan without undue experimentation. The response to treatment is monitored preferably after each dose using methods well-known in the art as well as those disclosed herein. The total duration of treatment and number of doses given depends on the response of the subject to the previous dose or doses.

Conventional routes of administration are used. An FcR-blocking effective amount (or a therapeutically effective amount as described above) of a polymer according to the invention is contacted with the target cells. By "FcR-blocking effective amount" is intended an amount which is effective in producing a statistically significant inhibition of a cellular activity mediated by an FcR. This may be assessed in vivo or in vitro using tests such as those listed below. Typically, FcR blockade is measured by assessing inhibition of phagocytic function or of the binding of immune complexes or monomeric SpA-Ig complexes.

Assessment of FcR Binding and Cell Activation

A number of assays are used to assess the binding of SpA polymers of the present invention to FcR and the inhibition of FcR binding of ligands or the activation of cells consequent to this binding, as follows:

1. Inhibition of EA rosette formation (Sulica, A. et al., *Scand. J. Immunol.* 5:1191 (1976); Ghetie, V. et al., *Scand. J. Immunol.* 5:1199 (1976);
2. Binding of Radiolabeled IgG-SpA complexes to cells including macrophages, lymphocytes or platelets (Sulica, A. et al. *Europ. J Immunol.* 9:979 (1979); Hawiger, J. et al., *J Clin. Invest.* 64:931 (1979));
3. Inhibition of C'-mediated immune lysis (Austin et al., *Infec. Immun.* 12:8211 (1975); Austin, R. M. et al., *J Immunol.* 117:602 (1976));
4. Inhibition of phagocytosis (Dosset, J. H. et al., *J Immunol.* 103:1405 (1969))
5. Antibody-dependent cellular cytotoxicity (ADCC) (Kay, H. S. et al., *J Immunol.* 118:2058 (1977));
6. Release of mediators (histamine and serotonin) from platelets after binding to the platelet FcR (Hawiger et al., supra).

The polymers and polymer conjugates may also be used in vitro to test products, monitor therapy, and diagnose diseases associated with abnormal function of Fc receptors or abnormal processing of immune complexes or FcR-binding structures. Thus, for example, it is possible to test whether a subject has a disease or a condition amenable therapy by the SpA polymers or polymer conjugates of the present invention. The subject's cells, e.g., peripheral blood lymphocytes, are analyzed in vitro for FcR function such as binding activity or immune complex uptake (see above) in the presence of a SpA polymer or polymer conjugate, preferably complexed with Ig). If the polymer or polymer conjugate inhibits FcR function, the subject is considered a good candidate for therapy, as it the therapeutic composition would inhibit pathogenic FcR-based effector functions (such as platelet opsonization in ITP or synoviocyte release of cytokines and degradative enzymes in RA). In this way, it may be possible to select among various polymers or polymer conjugates for a size and composition range and a dose range most likely to be efficacious in vivo. For monitoring therapy with the compositions of the present invention, one would assay FcR functions over time after administering the polymers or polymer conjugates. Additionally, cells bearing FcRs would be assayed for the presence of the polymer or polymer conjugates bound to the cell surface, for example, by conventional immunoassay. Decreases in the relevant FcR binding or post-binding effector function would prognosticate or corroborate therapeutic efficacy. Restoration of these functions over time would serve as a useful indicator of the need to prolong or reinstate therapy.

For the diseases or conditions described herein, administration of the composition is typically parenteral, for example, by subcutaneous (sc), intravenous (iv), intra-arterial or intramuscular (im) injection or infusion to a mammal, preferably a human. The polymer or polymer conjugate may be administered locally, regionally, systemically or a combination of the above to the subject to achieve a therapeutic response.

METHOD OF INFUSION OF POLYMERIC SpA OR A POLYMERIC CONJUGATE

The specified amount of a SpA polymer, preferably about 2–100 μg, is added to about 700 ml of human plasma that is diluted 1:1 with heparinized saline solution at room temperature.

Human IgG in a concentration of 500 μg/dl (in the 700 ml total volume) may also be used. The solutions are allowed to stand for about 1 hour at room temperature. The solution container may then be attached directly to an iv infusion line and administered to the subject at a preferred rate of about 20 m/min.

In another embodiment, polymeric SpA or a polymeric SpA conjugate is directly infused into a subject. The appropriate amount, preferably about 2–100 μg, is added to about 250 ml of heparinized saline solution and infused iv into patients at a rate of about 20 ml/min.

As with use of the SpA immunoadsorbent columns, the present composition can be given one time but generally is administered six to twelve times. The treatments can be performed daily but are generally carried out every two to three days or as infrequently as once a week, depending on the toxic effects observed in the patient.

MONITORING THE SpA IMMUNOADSORBENT COLUMN

The present invention provides an important adjunct method to be used in conjunction with conventional SpA immunoadsorbent column therapy. In this method, a SpA immunoadsorbent column is monitored to determine the amount of SpA inadvertently leached from the column into patient plasma which has been perfused over the column. The method is performed by withdrawing aliquots of plasma perfused over the column and measuring the concentration of SpA therein. Methods for assaying the SpA are conventional in the art and include ELISA assays using antibodies specific for SpA (see below).

This monitoring method permits the detection of dangerously high amounts of SpA in the plasma perfusate from a commercial SpA column which will permit a treating physician to make decisions regarding cessation or modification of therapy to avoid side effects. The optimal amount of SpA which should be infused into a subject per treatment is between about 2μg and 100 μg. The detection of higher levels in the plasma perfusate using the present monitoring method will serve as an indication that the treatment should be halted. The detection of levels below this range serve as an indication that effective therapy requires more, or more frequent, doses. Hence, methods of the present invention are directed to the combination of monitoring the eluates or perfusates of SpA columns and determining whether to infuse the material, deciding what dosage to administer, and otherwise modifying the previously used treatment protocols which did not take into consideration the presence of complexed or polymerized SpA and SpA-enterotoxin moieties derived from the use of the SpA columns.

Having now generally described the invention, the same will be more readily understood through reference to the following examples which are provided by way of illustration, and are not intended to be limiting of the present invention, unless specified. All temperatures are given in degrees Celsius and concentrations as weight percent unless otherwise specified.

EXAMPLES

The following studies evaluated the underlying basis for the therapeutic effects and the toxicities of SpA immunoadsorbent columns in current use. In particular, plasma that was perfused over a SpA immunoadsorbent column was evaluated for the presence of Staphylococcal products. More specifically, as set forth below, the post-perfusion plasma which is returned to the patient was found to contain Staphylococcal protein A (SpA) in higher MW polymeric form. A similar increase in SpA in the column perfusate was observed using fluids other than plasma, including protease-free albumin, guanidine HCl, $Na_2CO_3$, and acid-water, all of which acted as eluants of SpA from the columns.

EXAMPLE I

PREPARATION AND ELUTION OF THE PROSORBA® COLUMN

A SpA-silica immunoadsorbent column (Prosorba® column manufactured by the IMRE Corporation) which contained 256 ml of silanized silica to which SpA is immobilized via the carbodiimide method was used. This material which is FDA approved for treatment of ITP and hemolytic uremic syndrome was tested to identify the active agent or agents responsible for the therapeutic effects of these columns. The cartridge was opened, and three columns were prepared using 50 ml of silica per column. Each 50 ml aliquot of column material was placed in a 4×4 cm column and washed with 3 liters of normal saline at a flow rate of 20 ml/minute using a upward flow system as described in the manufacturer's instructions. The columns were perfused with one of the following materials:

(1) 1.5% human serum albumin (HSA; obtained from Sigma Chemical Co.) free of protease activity (assessed by the QuantiCleave® assay, Pierce Chemical).

(2) 1.5% HSA, 99% pure, protease-free by the fluorescent casein assay (obtained from ICN).

(3) Human plasma from a patient with ITP and from a normal donor was collected in acid citrate dextrose solution according to IMRE Corporation instructions and was stored at −20° C. until use.

(4) 6M guanidine HCl, pH 2.0, was used as a test eluant because it is a powerful chaotropic agent that disrupts electrostatic interactions and hydrogen bonding between various molecules and solid surfaces. Guanidine-HCI elutes proteins that are non-covalently bound to glass surfaces where acid alone may not be effective. Guanidine HCl does not denature SpA.

(5) Acid-water, pH 2.0 prepared and used according to Balint (5) removes non-covalently bound SpA from the SpA-silica matrix.

(6) $Na_2CO_3$ in 0.5 M NaCl, pH 10.5, was used to elute ionically bound SpA from the silica surface that was resistant to acid-water elution.

Samples (50 ml) of the above eluants were perfused through the columns at a flow rate of 3 ml/minute. The eluted samples (post- perfusion) were collected, pooled and assayed for SpA. Pre-perfusion samples were similarly assayed. Assays were performed using a SpA ELISA kit (Repligen) according to the manufacturer's instructions. A series of standards were prepared by serial dilution of the recombinant SpA solution supplied. The concentrations of SpA used in the assay were 1.62, 0.81 0.405, 0.2, 0.1, 0.05 and 0.025 ng/ml. The various sample eluates prepared in Example 11 were serially diluted (with the kit assay diluents) to the following concentrations: Undiluted, 1:1, 1:3, 1:7, 1:15, 1:63, and 1:127. (As used herein, a 1:3 1 dilution means that 1 part of sample is diluted with 31 parts of diluent. Thus, a 1:31 dilution results in a solution that is 1/32 as concentrated as the original solution).

For the plasma and HSA eluate samples, the 1:127 dilutions were omitted and replaced by blanks. The plasma blank and the HSA blank consisted of undiluted plasma and 10 mg/ml of HSA in PBS, respectively. The blanks had not been passed over the SpA columns and were used as controls in the ELISA assay to document that positive results in the eluates were due to the presence to SpA. These samples were analyzed with eluates of Prosorba® columns described in Example II.

EXAMPLE II

ELUTION OF THE PROSORBA® COLUMN MATERIAL

Prosorba® column material was perfused with various eluants as described in Example I. After washing the columns, the eluates were passed over the columns in 15 ml volumes, and the pre- and post-perfusion solutions were evaluated for the presence of SpA as described above.

RESULTS

The results of the first study are given in Table 3 below. Eluates were pooled and tested for SpA. Normal human plasma and plasma from a patient with ITP eluted SpA to a similar degree (12.31 and 15.63 ng/ml, respectively). Guanidine HCI, pH 2.0 also eluted up to 70% of the level eluted by plasma. Human albumin (1.5%; protease free), even at a concentration 50% below that of usual plasma levels, still eluted more than 50% as effectively as did whole plasma.

This study was repeated using protease-free human albumin 90/o pure (ICN) and the same protease-free albumin with the serine protease inhibitor Pefabloc SC® (Boehringer-Mannheim) added. The results (Table 4) show that 6.14 ng/ml of SpA leached with the protease-free albumin and 11.69 ng/ml was released when Pefabloc was added.

TABLE 3

| Eluant | SpA (ng/ml) |
|---|---|
| Human Plasma (normal) | 12.31 |
| Human Plasma (ITP) | 15.63 |
| Human Albumin (protease-free) | 7.98 |
| 6M guanidine HCl, pH 2.0 | 10.74 |

50 ml of samples were perfused over Prosorba ® column (50 ml). Eluates were pooled and tested for SpA. Pretreatment samples had no detectable SpA.

To determine the amount of SpA released after perfusion of an entire Prosorba® column as used clinically, an experiment was designed using 3000 ml of heparinized saline wash of the full Prosorba® column followed by infusion of 250 ml of patient plasma followed by a 500 ml saline wash. Pre- and post-perfusion samples were collected and assayed for SpA content. Results (Table 4) show comparable amounts of leaching from the whole system as in the model system. The total amount of SpA leaching, corrected for the 750 cc perfused into patient, is 5 μg. Nearly the same amount of SpA eluted with the heparin saline wash (0.83 ng/ml) which when corrected for the 3000 cc of saline perfused amounts to 2.5 pg of released SpA (Table 4). An additional study confirmed the elution with 6M guanidine HCI pH 7.0, which was 60% of the elution seen with 6M guanidine HCI, pH 2.0.

TABLE 4

| ELUANT | SPA (ng/ml)[1] |
|---|---|
| Heparinized saline wash (3000 cc) | 0.83* |
| Heparinized Plasma (750 cc) | 16.9* |
| Human Albumin (Protease Free-ICN) | 6.14** |
| Human Albumin (Protease-Free plus Pefabloc) | 11.69** |
| 6M guanidine HCl (pH 7.0) | 10.64 |

[1]Pre-treatment levels of SpA were always 0
*Whole Prosorba ® column
**Model system The effect of pH on elution from the Prosorba® column was evaluated. Results (Table 5) show significant leaching with acid-water. This was very surprising given that the column had purportedly been treated with acid water during the preparation process to remove non-covalently bound SpA (5). Moreover, significant leaching occurred with $Na_2CO_3$ perfusion. Both buffers eluted non-covalently bound SpA, confirming the effects seen with protease-free HSA.

TABLE 5

EFFECT OF pH ON SpA ELUTION

| Sample | Post Perfusion SpA (ng/ml) |
|---|---|
| Acid-water, pH 2.0 | |
| 1) Heparin Wash | 0.34 |
| 2) Fraction 1 | 2.72 |
| 3) Fraction 2 | 8.67 |
| 4) Fraction 3 | 2.28 |
| 5) Fraction 4 | 0.49 |
| $Na_2CO_3$, pH 10.5 | |
| 1) Fraction 1 | 24.42 |
| 2) Fraction 3 | 87.71 |

PRESENCE OF ENTEROTOXINS IN SpA COLUMN ELUATES

The $Na_2CO_3$ eluate of the Prosorba® column was analyzed for the presence of Staphylococcal enterotoxins. The eluate was divided into three aliquots of 1 ml each and was treated as follows:

Aliquot #1: 16 hr treatment with 100 μl 10X Trypsin (Gibco-BRL, Gaithersburg, Md.) with shaking at 60 rpm at room temperature.

Aliquot #2: 4 hr treatment as above.

Aliquot #3 control, treated with 100 μl of PBS-Tween.

Prior to testing, all three aliquots were treated with normal rabbit serum. Testing was performed in an ELISA using affinity-purified IgG antibodies specific for Staphylococcal enterotoxin A, B, C or D (SEA, SEB, SEC, SED). Polystyrene beads were coated with one of the above antibodies or were uncoated (negative control). For capture of enterotoxins, antibody-coated or control beads were added to samples of the above three groups, and the mixtures were shaken overnight. On the next day, the beads were removed and washed. Immobilized enterotoxins were detected using the same antibodies conjugated to alkaline phosphatase. Antibody-alkaline phosphatase complexes were added to all the bead samples, and after incubation, paranitrophenyl phosphate (PNPP), a chromogenic substrate for alkaline phosphatase, was added and allowed to generate colored product. The colored reaction product was quantitated by absorbance at 405 nm ($A_{405}$). The results are shown in Table 6.

TABLE 6

| Eluate | | $A_{405}$ after reaction with antibody to: | | | | |
|---|---|---|---|---|---|---|
| Aliquot | Treatment | SEA | SEB | SEC | SED | Control |
| #1 | Trypsin, 16 hrs | 0.007 | 2.038 | 0.048 | 0.010 | 0.009 |
| #2 | Trypsin, 4 hrs | 0.245 | 0.909 | — | — | 0.048 |
| #3 | PBS-Tween | 1.181 | 0.307 | 0.363 | — | 0.034 |
| SEB | Standard (1 ng/ml) | — | 0.401 | — | — | 0.015 |

The results show that aliquots #2 and #3 were positive for the presence of SEA, SEB and SEC. Aliquot #1 appeared positive for only SEB after overnight trypsin treatment. It was concluded that carbonate elution of the Prosorba® column resulted in the emergence of at least three different Staphylococcal enterotoxins.

EXAMPLE III

A. Preparation of the Derivatized Silica Matrix

The following protocol was used to modify a silica matrix with 3-aminopropyltriethoxysilane to obtain a primary amine on the silane surface for carbodiimide coupling of SpA to the silane. Chromosorb P (Sigma Catalog No. C5889), a dry, brown powder with the consistency of fine sand, is a diatomite support that can be used for both analytical and preparative scale chromatography primarily for hydrocarbons and compounds of low porosity. The silica matrix was suspended in deionized water as 50% (v/v) solution and placed in a suction-filtered flask. The flask was stoppered, and vacuum was applied while the support was gently mixed to remove air bubbles from the inner pores and to fully hydrate the silica matrix.

The silica matrix slurry was then transferred to a sintered glass Buchner filter funnel and, the matrix material was washed with about 5 liters of deionized water until there was no evidence of fines coming through the filter. The water-washed silica was further washed with 5 liters of acetone to remove most of the water. One aliquot of the support material was then suctioned dry. As the acetone evaporated from the silica matrix, the support was gently dispersed with a spatula to allow the inner surfaces to dry without caking. The support was then transferred to a 2 liter rotary evaporator flask, and the silica matrix covered with toluene. Vacuum was applied as the support was rotated to remove entrapped air in the pores of the silica matrix. The flask was then heated to 60° C. under vacuum to distill the toluene from the silica matrix. This process causes any remaining water to azeotropically cool-distill with toluene, thus removing the final traces of water from the support. After about 1 hour of slow distillation, no more water was seen azeotroping with the toluene. (The failure to completely remove water can cause the silane to polymerize in the pores of the silica, thus clogging the pore structure).

The dried silica matrix was then suspended in 1 liter of toluene containing 10% 3-aminopropyltriethoxysilane (Aldrich Chemicals) and slowly rotated overnight at room temperature. The particles of silica matrix were transferred to a Buchner filter as above. The derivatized silica matrix was washed extensively with acetone until no evidence of amines leaching off the silica matrix was observed. Approximately 10 liters of acetone were required for this wash. Amines were detected using trinitrobenzene sulfonate (TNBS) as a 5% ethanolic 20 solution. An aliquot of the wash (1 ml) was added to a test tube containing about 2 ml of saturated sodium borate solution. Several drops of TNBS solution was added to this mixture. The presence of an orange color (changed from the original yellow color of TNBS) indicated the presence of amines. The silica matrix was then suctioned dried of excess acetone within the Buchner funnel, transferred to the suction filter flask, and a vacuum was applied to remove the last traces of acetone. The final aminopropyl silica matrix weighed 978 gm.

B. Preparation of SpA on Aminopropyl-Silica

One gm of SpA was obtained from Pharmacia (bulk product No. 17-087201; Staphylococcus aureus, Cowan 1 strain). Carbodiimide coupling was used to link the carboxyl groups on the SpA molecule and the amine group of the silica matrix. Carbodiimide activates the carboxylate groups to intermediate esters which are highly reactive to nucleophiles. The amine groups on the silica matrix attack this ester causing the carbodiimide to leave as a soluble isourea compound resulting in an amide linkage with the protein. This reaction also allows the polymerization of SpA due to the presence of free amine groups. This side reaction was determined to be a major difficulty in using carbodiimide to couple protein to the derivatized support.

C. Ratio of Reactants

As disclosed by Balint et al. (1987, supra), the coupling of the SpA to the silica matrix is carried out with the matrix at a loading level of 2g of protein per kg dried aminopropyl silica. Fifty g carbodiimide (CMC, 1-cyclohexyl-3-(2-morpholinoethyl) carbodiimide trimetho-p-toluenesulfonate salt; MW=423.58) were added to this mixture. This represents 0.11 moles of the CMC per kg of silica matrix.

In the present studies, the more commonly used carbodiimide EDC (1-ethyl-3-(3-dimethyaminopropyl carbodiimide) was substituted for CMC. CMC and EDC are both water soluble and have virtually the same properties in forming amide bonds between carboxylates and amines. Since the MW of EDC is 191.7 (as the HCl salt), the amount required per kg of silica matrix is 22.6 gm to obtain the same ratio of reactants as disclosed by Balint et al. (supra) using CMC.

D. Efficiency of Coupling

To determine the efficiency of SpA coupling to the aminopropyl silica support, a test batch was made using 1 gm of derivatized silica matrix. Deionized water (1 liter) was adjusted to pH 3.5 with dilute HCI. Aminopropyl silica (1 gm) prepared as described above, was placed in a suction filter flask (10 ml) and suspended as a 50% slurry in the acid water. A vacuum was placed on the flask and the silica matrix was gently mixed to remove entrapped air. The hydrated silica matrix (approximate 2 ml) was transferred to a 5 ml polypropylene minicolumn containing a porous polyethylene bottom disk.

The support was washed extensively with acid water until the pH of the eluate was 3.5. Since the amines contributed to a highly basic charge on the gel, about 25 ml of acid-water was required to titrate all the groups to the appropriate pH. After washing, the silica matrix was drained of excess water, but not allowed to dry. A bottom cap was placed on the column to prevent further flow.

SpA (2 mg) was dissolved in 1 ml of the acid-water. The absorbance of this solution at 275nm was 0.320. An absorbance scan of this solution gave the characteristic multi-peak pattern of SpA with an absorbance maximum at 275nm. The SpA solution was added to the silica matrix in the column and gently mixed. EDC (22.6gm in 1 ml of acid water was added to the silica matrix SpA mixture). A top cap was placed on the column. The silica matrix was then suspended by gentle inversion and the entire column rocked using an end-over-end rocker. The reaction was continued for 24 hours at room temperature.

After the reaction, the column was drained, and the solution was measured for absorbance at 275 nm (as a measure of the presence of protein). The total absorbance had actually increased to 0.366. An absorbance scan of this solution indicated no protein peak at 275 nm, but the shoulder of a larger peak at lower wavelengths was contributing to the absorbance at this wavelength. The isourea byproduct of the EDC reaction may have contributed to the absorbance increase. Following dialysis against 10 mM sodium phosphate, 0.15M NaCl, pH 7.2 (PBS) overnight at room temperature to remove any low molecular contaminants, the larger peak was still present at lower wavelengths. Since the low molecular weight isourea product of the EDC carbodiimide reaction was soluble, it should have been completely removed by dialysis. Therefore, the peak was not due to the presence of a low molecular weight isourea product.

The polymerization of SpA into large molecular weight species also contribute to this finding. There was no indication that any SpA remained uncoupled after the reaction. Thus, immobilization either by non-covalent adsorption or covalent binding occurred with nearly 100% efficiency.

E. Large Scale Preparation of Immobilized Protein Silica Matrix

The following procedure was used to produce a large batch of SpA-silica matrix for use in these studies.

Ten liters of deionized water was adjusted to pH 3.5 with dilute HCl to form acid-water. Aminopropyl-silica matrix (100 gm), was placed in a suction filter flask and sufficient acid-water added to make a 50% slurry. A vacuum was applied to the slurry to remove entrapped air from the pores while the support was gently mixed in the flask. The matrix was transferred to a Buchner filter and washed with acid-water until the pH of the washes equaled 3.5. Several liters of acid-water were required to titrate the basic amine groups on the matrix down to the reaction pH.

The silica matrix was drained of excess acid-water to obtain a wet cake. SpA (224 mg) was dissolved in 20 ml of acid-water. The absorbance at 225nm was 1.438. The scan displayed the characteristic peaks of purified SpA. The SpA solution was added to the washed aminopropyl-silica matrix support along with sufficient acid-water to obtain a 50% slurry. EDC (2.26 gm) was added to the slurry with gentle mixing to suspend the gel and dissolve the carbodimide to form a reaction mixture. The reaction mixture was mixed overnight at room temperature using an orbital shaker.

After 24 hours, the reaction mixture was transferred to a Buchner funnel with the glass filter pad and drained of excess solution. The post-coupling reaction solution was analyzed for the presence of uncoupled SpA using an absorbance scan. There was no evidence of a protein peak at absorbance of 275nm. The absorbance at 275nm after coupling was 0.082. This was due to a shoulder from the lower molecular weight peak (which was not attributable to SpA).

The SpA coupling was extremely efficient. The gel was washed extensively with deionized water and then suspended in an equal volume of acid-water, pH 2.5, for 5 minutes at room temperature as described by Balint et al. (1987, supra). After this treatment, the gel was drained of acid water. The drained gel was measured by absorbency scan, but no evidence of a SpA peak was observed. The gel was then washed with water and finally stored at 4° C. in water containing 0.02% sodium azide as a preservative.

F. Elution of SpA Silica Column (Table 7)

Using the large scale batch of immobilized SpA silica matrix prepared in Section E, both HSA and human plasma eluates showed the presence of SpA. By linear regression analysis of the standard curves, the HSA sample contained 13.96 ng/ml SpA and the plasma sample contained 22.88 ng/ml SpA. Five ml of derivatized silica matrix were used for this study, and 5 ml of each eluant were perfused over it. By extrapolation to a 50-fold increase in eluant and silica matrix, as the system is used clinically, the HSA eluate contained a total of approximately 0.698 pg SpA while the plasma contained a total of approximately 1.14 $\mu$g SpA (Table 7).

TABLE 7

ELUTION FROM SpA SILICA COLUMN

| TREATMENT | SpA | Total Eluate SpA |
|---|---|---|
| 1) Human Plasma | 13.96 ng/ml | 0.698 $\mu$g |
| 2) Human Albumin | 22.88 ng/ml | 1.14 $\mu$g |

G. Large-Scale Elution of the Prosorba® Column

To analyze leached protein coming off the IMRE SpA-silica support, a large column was packed and treated with high pH carbonate buffer. This buffer was shown to result in the greatest degree of leaching from the support.

IMRE SpA silica support (250 ml) was packed into a column and stirred gently with 0.15 M NaCi solution to remove air. As a pre-treatment, the column was washed with 1 liter of saline and the eluate discarded. The column then was eluted with 3×250 ml of 0.2M $Na_2CO_3$, 0.5M NaCl, pH 10.5. The eluted fractions were collected in plastic bottles and stored at 4° C. overnight. The carbonate-eluted fractions were pooled and dialyzed against deionized water to lower the pH (4 changes, 20 liters each, 3 days at 4° C.). The dialyzed solution was then concentrated using Amicon Centri-Prep units with a molecular weight cut-off of 10 kDa. The resultant solution was analyzed by absorbance scan. A small amount of 280nm absorbing material was observed.

H. Gel Filtration of the Eluted Samples

A Waters 650E Chromatography System with Superose 6® (Pharmacia) size exclusion column was used to analyze the samples from the above experiments. The chromatography buffer was 0.1M sodium phosphate, 0.15 M NaCl, pH 7.5. The gel filtration was done at a flow rate of 0.5 ml/min, and peaks were detected by monitoring the absorbance at 280nm. The concentrated eluant from the Prosorba® column was injected at 200 $\mu$l due to its dilute nature.

Figure 3:
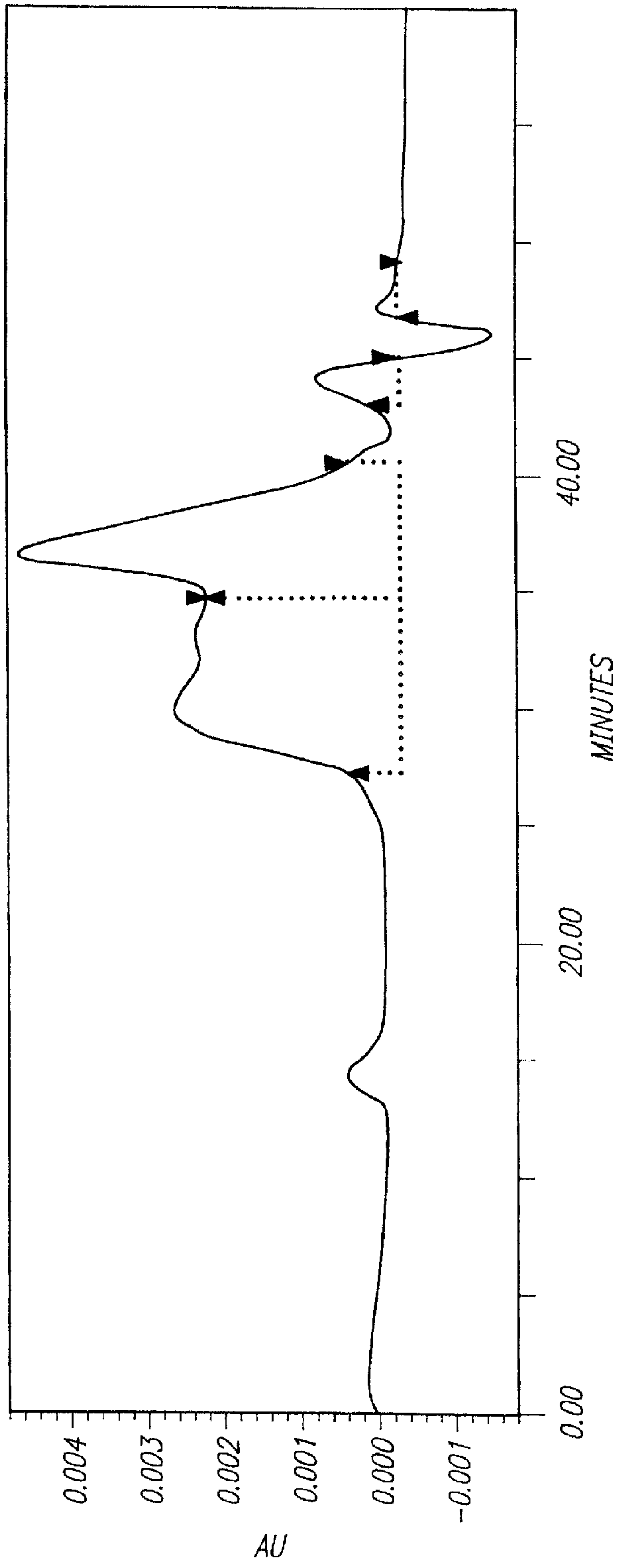
FIG. 3 is a chromatogram showing the concentrated column eluate from the IMRE column using carbonate buffer was analyzed by gel filtration on a Superose 6 FPLC column. Sample size was 200Tl and the elution monitored at 280nm. Peaks eluting at several molecular weights, including a small one at high molecular weight, indicates polymerized protein leaching from the SpA cartridge.
Figure 4:
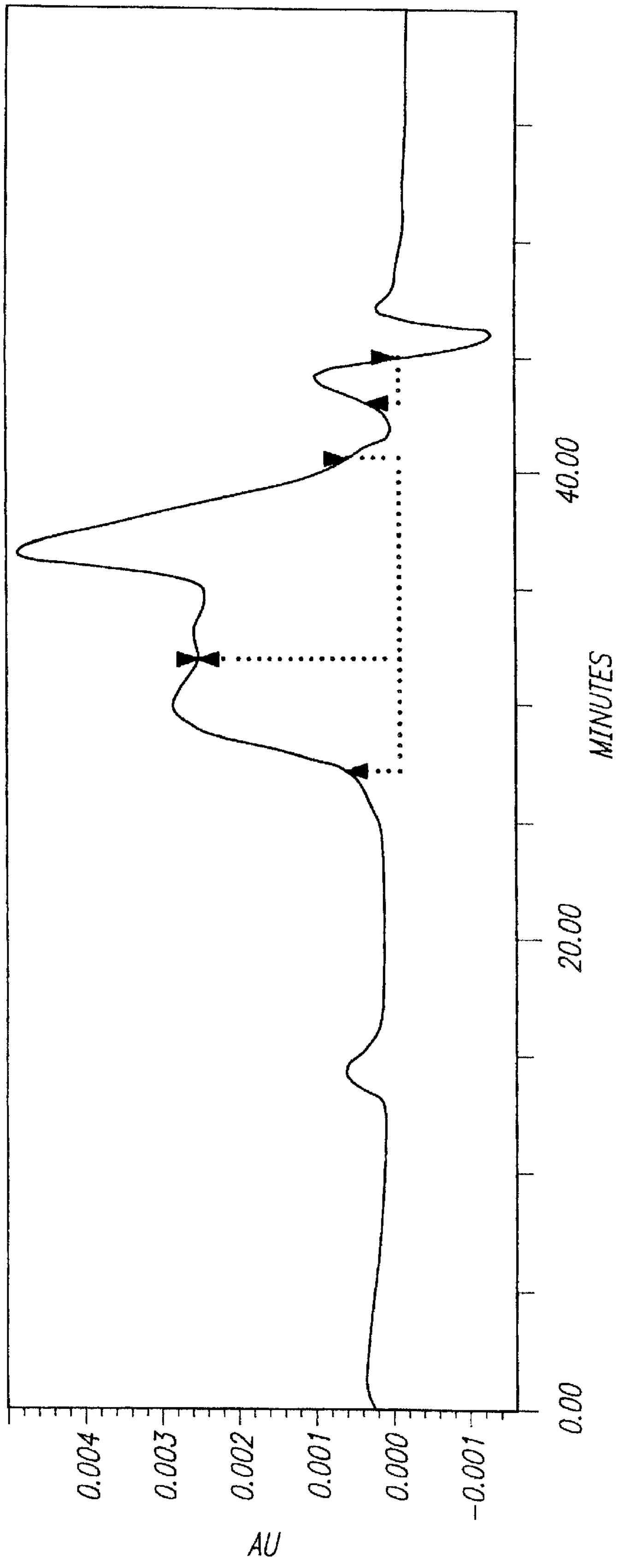
FIG. 4 is a chromatogram showing a repeat of the chromatography shown in FIG. 3, demonstrating the reproducibility of the gel filtration separation.
Figure 5:
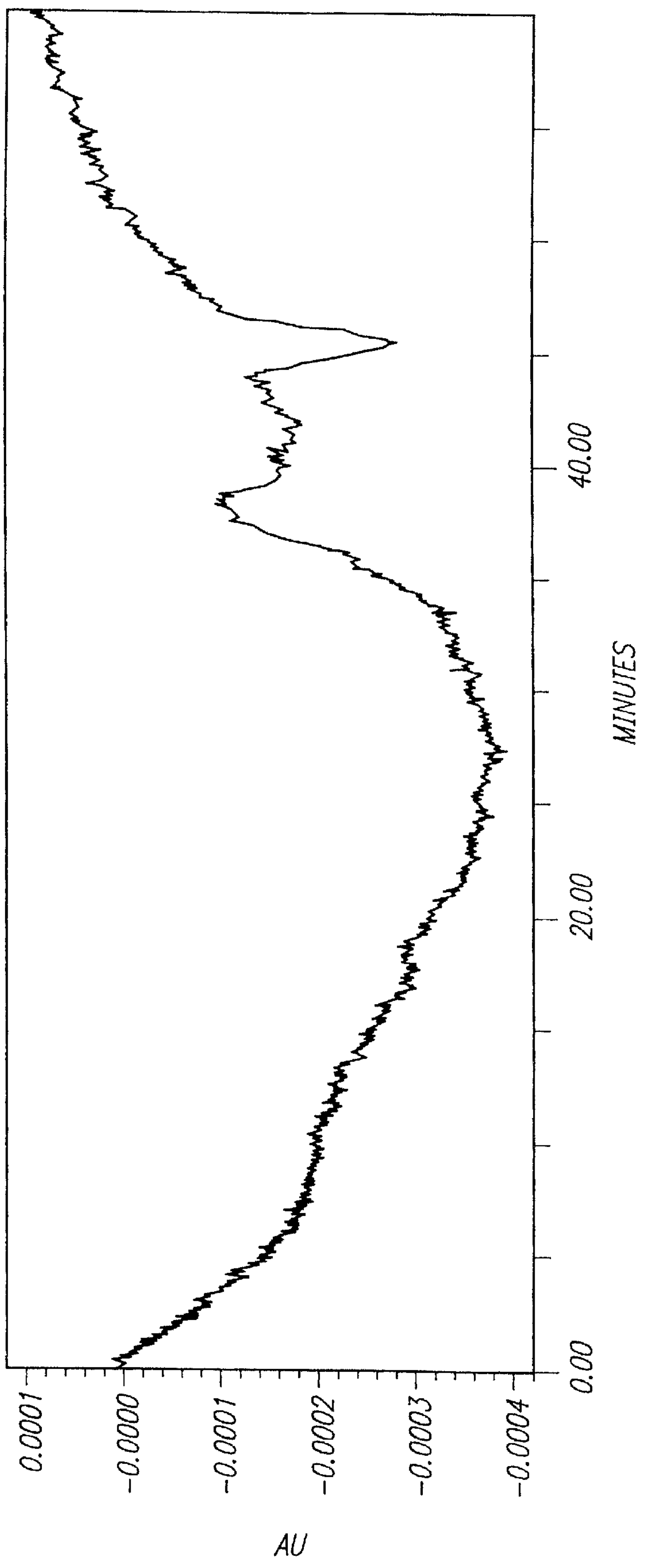
FIG. 5 is a chromatogram showing gel filtration analysis of sample IR (Example III and Table 8) which contained 2mg of SpA plus 2 μg of SEB that was reacted with 1-ethyl-3-(3-dimethyaminopropyl carbodiimide (EDC). Most of the protein material applied to the column did not elute, indicating extremely large molecular weight material was formed by the polymerization process. Note some material did elute at a point corresponding to the elution of carbonate-leached material from the IMRE cartridge (compare FIG. 2).
Figure 6:
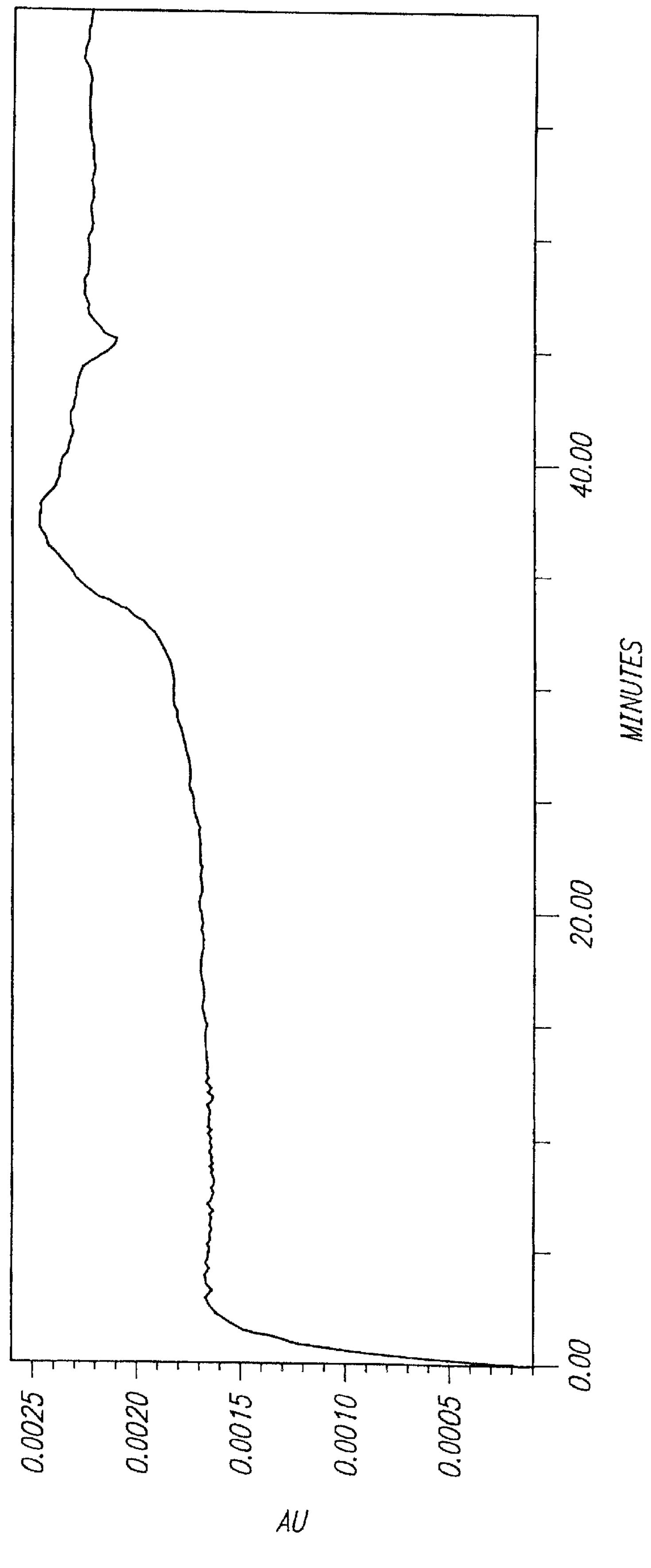
FIG. 6 is a chromatogram showing gel filtration analysis of sample 2R (Example III and Table 8) which contained 2mg of SpA plus 10 μg of SEB that was reacted with EDC. Most of the protein material applied to the column did not elute, indicating extremely large molecular weight material was formed by the polymerization process. Note some material did elute at a point corresponding to the elution of carbonate-leached material from the IMRE cartridge (compare FIG. 2).

The chromatogram appears in FIG. 1. SpA showed a single sharp peak without significant shouldering. However, the concentrated eluate from the Prosorba® column showed a broad combination of peaks in the region in which SpA and SEB would normally elute (FIG. 3). It also shows a small peak eluting earlier and consisting of high molecular weight material. It should be noted that very high MW material which may have been present in the carbonate buffer-eluted fractions might not have emerged from the gel filtration column. This was observed in the EDC-polymerized SpA/enterotoxin complexes (discussed below), wherein most of the material absorbing at 280nm was retained on the gel and did not come off the column. Therefore, very high molecular weight complexes are present but cannot be resolved using this method.

I. Preparation of Polymerized SpA

It was apparent that SpA was emerging from the Prosorba® column in polymerized form after elution with carbonate buffer. This could be explained by self polymerization of SpA by carbodiimide in the column preparation and its subsequent non-covalent adsorption to the silica surface. This eluted SpA polymer was the agent most likely to induce the reported therapeutic effects. In order to prepare polymerized, crosslinked SpA, EDC was utilized. SpA (Pharmacia) was dissolved at a concentration of 4mg/ml in 0.1M MES, pH 4.7 (actual solution: 26.45mg SpA in 6.59ml buffer). After the addition of 10mg EDC to each of the indicated tubes (see Table 8), the solutions were mixed and reacted for 2 hours at room temperature. Each solution was then transferred to an individual dialysis cassette and dialyzed to remove excess EDC and reaction by-products. The samples were dialyzed against 10 MM sodium phosphate, 0.15 M NaCl, pH 7.4 (1 liter, 4 changes, 2 days at 4° C.). No precipitation was observed in any of the samples after the crosslinking reaction was complete or after dialysis. After dialysis, each sample was transferred to a labeled microfuge tube and stored at −20° C.

Figure 2:
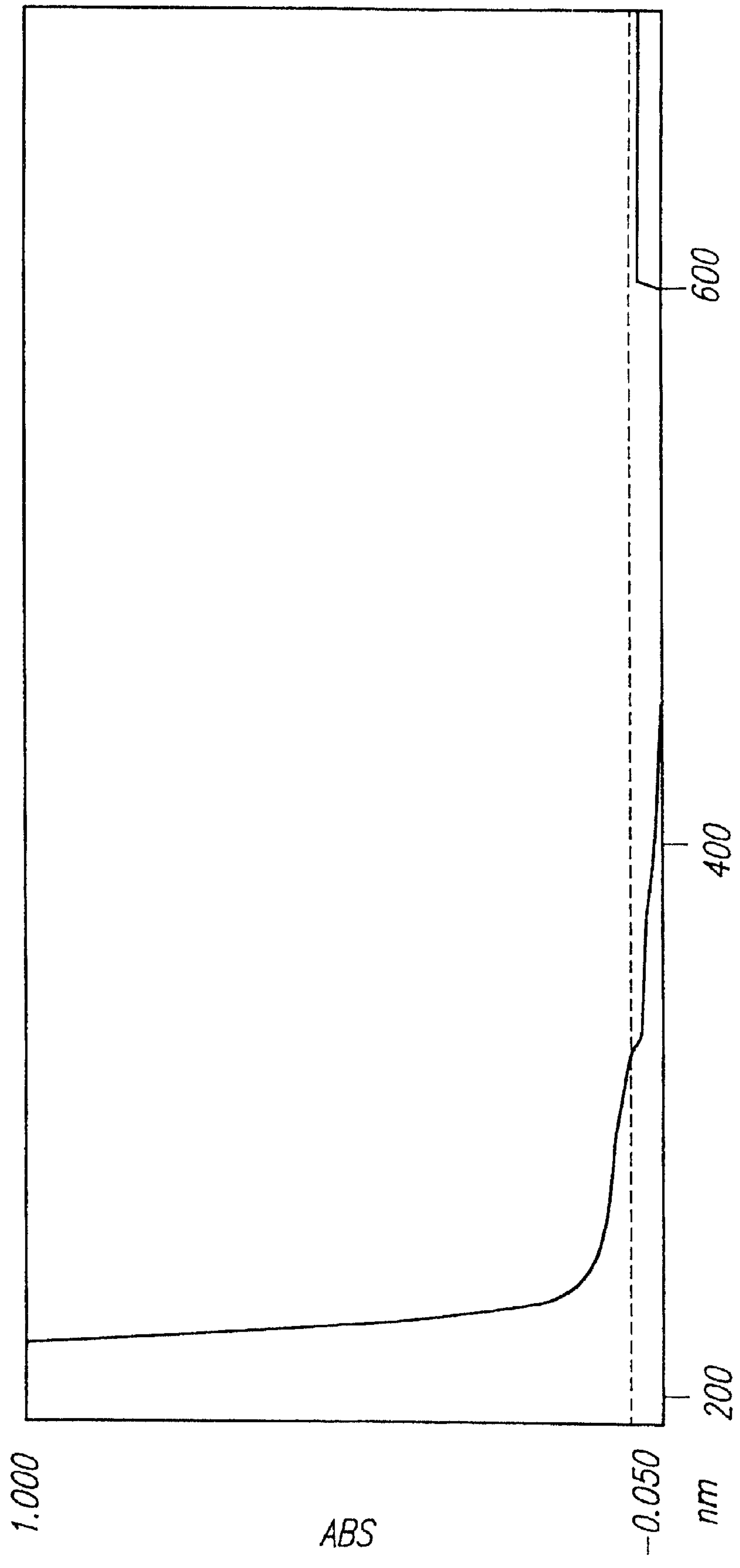
FIG. 2 shows the absorbance scan of the concentrated elution fractions from the IMRE SpA cartridge using 0.2M sodium carbonate, 0.5M NaCl, pHI10.5. A small amount of absorbing material at 280 nm (0.040) was evident. This concentrated material was used in the accompanying gel filtration analysis profiles.

The sample containing unreacted SpA showed a distinct peak upon gel filtration analysis (FIG. 2). However, upon crosslinking, this peak was not apparent. Although some material eluted at this point, it was a very small quantity and was not resolved into separate components. By absorbance scan there was a considerable amount of protein present in the conjugated samples (e.g., tube 3R gave an $A_{280}$ of 0.450), but the protein did not come out of the Superose column. This can only mean that the EDC conjugation was very efficient and formed large molecular weight complexes which were trapped in the gel filtration column (FIG. 2).

J. Preparation of SpA-Staphylococcal Enterotoxin B (SEB) Polymeric Conjugates

SpA was dissolved in the same buffer as above. One mg of SEB (from Toxin Technology) was dissolved in 1 ml of deionized water. Microfuge tubes were used as reaction vessels for the crosslinking procedure. The SpA and SEB solutions were mixed as indicated in Table 8 prior to initiating the reaction with EDC. The EDC was then added to the tubes indicated. As controls, the two proteins were mixed in the same ratios in the absence of added EDC. Note that three different amounts of SEB were added, resulting in three different SEB concentrations in the reaction solution. This resulted in SpA/SEB concentration ratios of 1000, 200 and 100 in the reaction mixtures. A reaction control of SpA alone was also included (Table 8).

TABLE 8

| Tube | SpA (μl) | SEB (μl) | EDC (mg) |
|---|---|---|---|
| 1 | 500 | 2 | — |
| 1R | 500 | 2 | 10 |
| 2 | 500 | 10 | — |
| 2R | 500 | 10 | 10 |
| 3 | 500 | 20 | — |
| 3R | 500 | 20 | 10 |
| 4 | 500 | — | — |
| 4R | 500 | — | 10 |

Figure 7:
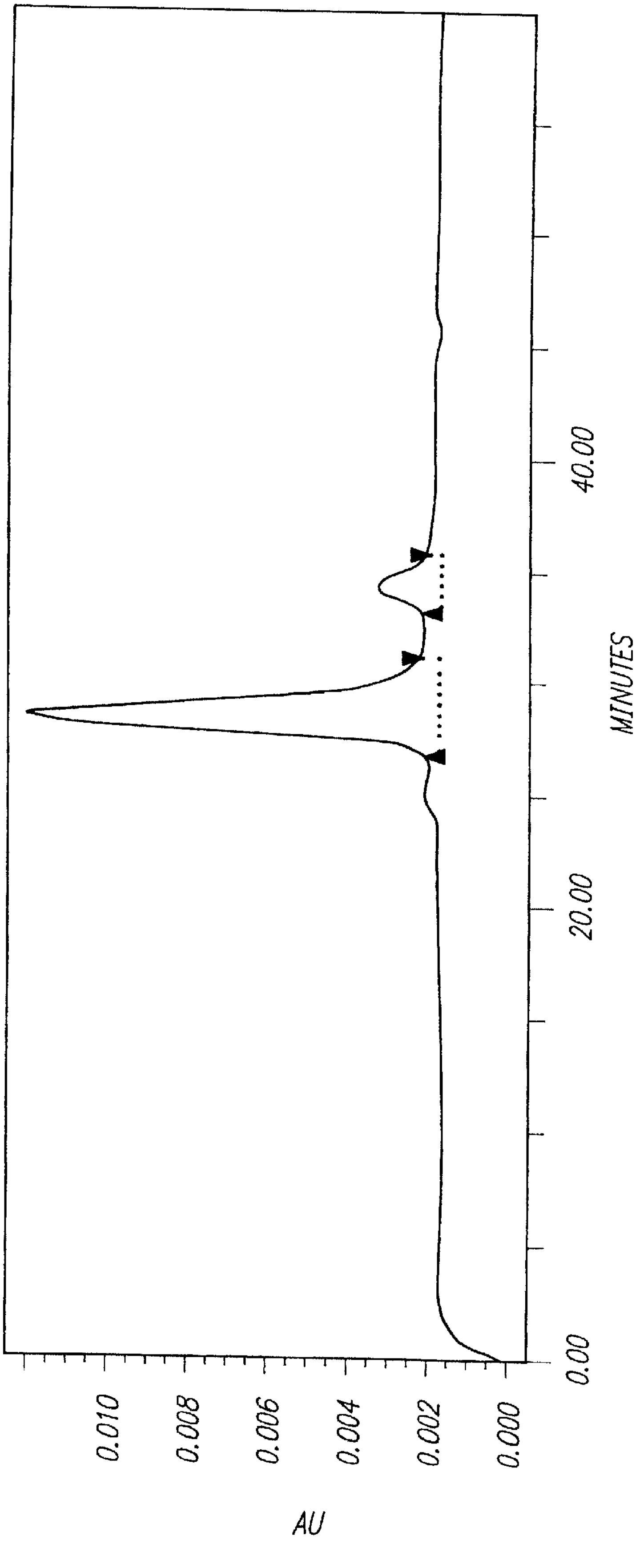
FIG. 7 is a chromatogram showing gel filtration separation of SpA (2mg) mixed with SEB (20 μg). 200 μp of this solution was applied to the column to indicate the elution positions of these proteins when mixed without EDC. SpA was the first peak eluting from the column, and SEB was the second.
Figure 8:
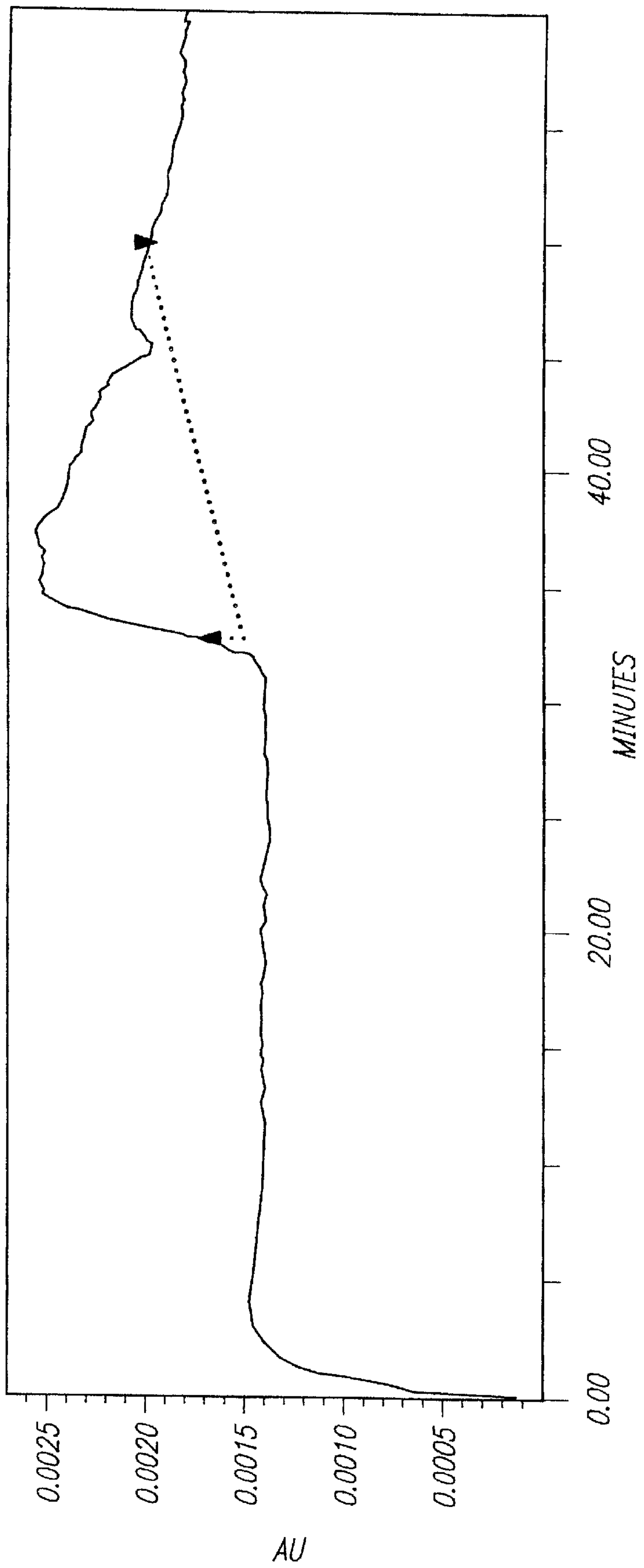
FIG. 8 is a chromatogram showing gel filtration analysis of sample 3R (Example III and Table 8) which contained 2 mg of SpA plus 20 μg of SEB that was reacted with EDC. Most of the protein material applied to the column did not elute, indicating that extremely large molecular weight material was formed by the polymerization process. Note some material did elute at a point corresponding to the elution of carbonate-leached material from the IMRE cartridge (compare FIG. 2).
Figure 9:
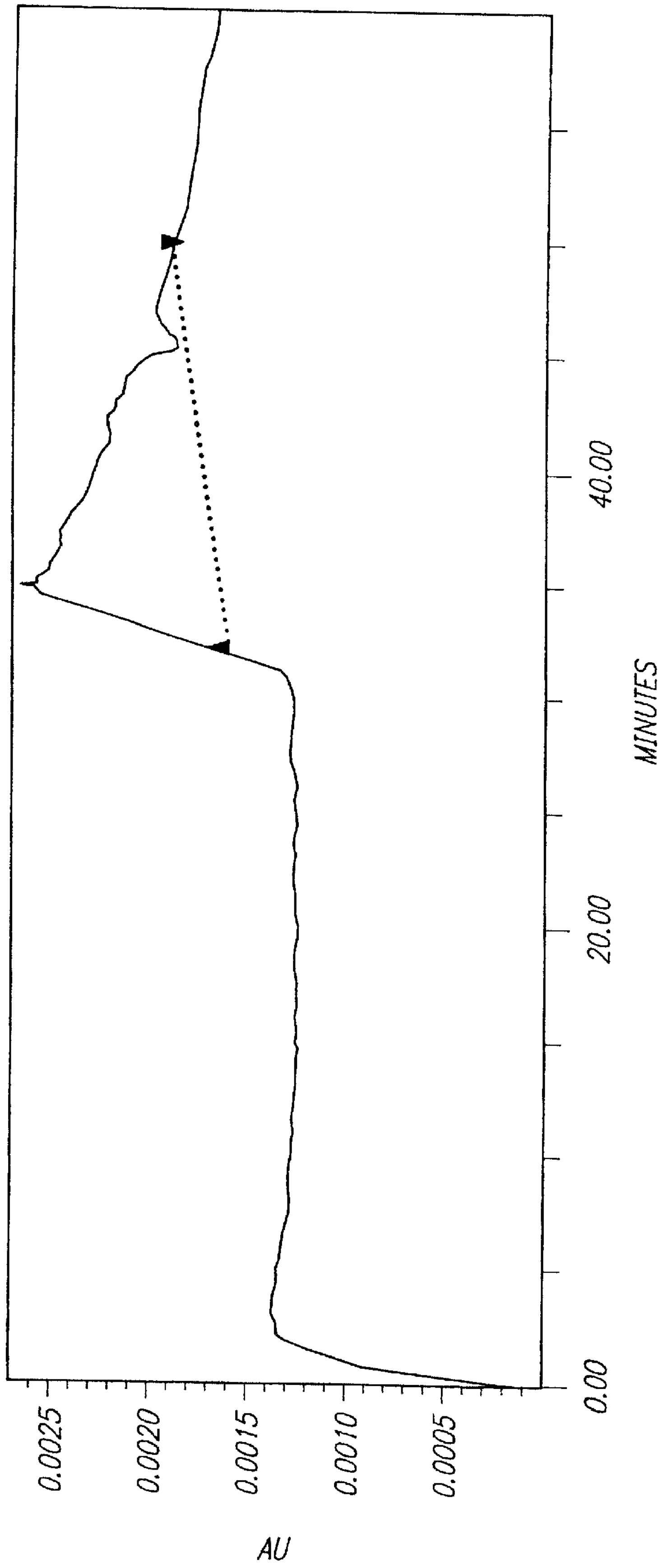
FIG. 9 is a chromatogram showing gel filtration analysis of sample 4R (Example III and Table 8) which contained 2mg of SpA that was polymerized by EDC. Most of the protein material applied to the column did not elute, indicating that extremely large molecular weight material was formed by the polymerization process. Note some material did elute at a point corresponding to the elution of carbonate-leached material from the IMRE cartridge (compare FIG. 2).

The EDC addition, incubation conditions and dialysis steps were carried out as described in Section I, above. The results of the chromatography experiments are described below. Control samples (SpA/SEB without EDC) were analyzed by gel filtration. The sample containing free SpA and SEB (Tube 3) showed two distinct peaks, the first being SpA and the second, SEB (FIG. 7). The EDC-crosslinked SpA/SEB (Tubes 1R, 2R and 3R) or SpA (Tube 4R) showed sharp peaks with a broad shoulders quite distinct from the free SpA and highly suggestive of an efficient SpA crosslinking to itself and/or to SEB (FIGS. 5,6,8,9). Identification of SEB in the conjugates was done by ELISA as described herein.

K. The Preparation of High Molecular Weight Covalently Polymerized SpA-IgG Complexes The Prosorba® column "off line" method of therapy involves ex vivo perfusion of the column with plasma which has been collected from the patient by phlebotomy. Hence, any SpA leaching from the column is mixed with autologous plasma, becomes complexed with IgG as very large molecular weight complexes, and is inadvertently infused into patients in this form (SpA-IgG complexes).

The present inventor created such complexes deliberately by adding polymerized SpA to either plasma or to a preparation of purified IgG. The amounts of plasma and IgG used were determined based on the quantities in the plasma used to perfuse a Prosorba® column "off line" and subsequently to infuse into a patient. This amount was calculated to be 700 ml of plasma which, in the process of perfusion, is diluted about 1:2 or 1:3 with heparinized saline present in the perfusion system.

L. Protection from the Adverse Effects of Staphylococcal Enterotoxin B by Covalently Linking SPA Adverse effects of SEB administered parenterally in animals and man have been well documented. These effects include hypotension, respiratory distress, nausea, vomiting and lethal shock. SpA preparations manufactured by purification of the protein from bacterial sources (in contrast to recombinant methods) are contaminated with enterotoxins ranging in concentration from 0.001 to 0.0001% (w/w).

With only 1–5 mg of immobilized SpA in a non-covalent system such as Prosorba®, the release of enterotoxin B resulted in significant cardiopulmonary toxicity, as previously described (Young, J. B. et al., *Amer. J Med.* 75:278 (1983)). In contrast, the by covalently crosslinking the SpA, any free SEB molecules (or other enterotoxins) are crosslinked or polymerized with the SpA, with themselves or with other enterotoxins in the preparation. Such crosslinking results in a molecular entity which would sterically hinder recognition and biological activity of the native enterotoxin molecules. Table 9 shows the amounts of SEB detected in the preparations described in Table 8, above.

Covalent crosslinking of SEB and SpA using the carbodiimide EDC reduced the amount of detectable SEB by 1000-fold compared to unreacted native molecules before crosslinking (Table 9). Hence, a major advantage of the covalently crosslinked polymers and polymer conjugates of the present invention in comparison to currently used SpA immunoadsorbent columns is the significant reduction in toxicity of the preparation caused by contaminating enterotoxins which invariably leach from the columns.

TABLE 9

ANALYSIS OF SEB LEVELS IN UNCONJUGATED AND CROSSLINKED SEB PREPARATION

| Sample | SEB added (μg) | SEB detected (ng) |
|---|---|---|
| I. UNCONJUGATED SpA* AND SEB | | |
| 1 | 2 | 100–150 |
| 2 | 10 | >1000 |
| 3 | 20 | >1000 |
| 4** | unknown | 5–10 |
| 5 ($Na_2CO_3$) | unknown | none |
| II. CROSSLINKED SpA-SEB (using EDC) | | |
| 1R | 2 | 5–10 |
| 2R | 10 | 30–40 |
| 3R | 20 | 40–50 |
| 4R* | unknown | 10 |

*Starting material was 2 mg of SpA
**Pharmacia SpA

EXAMPLE IV

Effect of the SpA Polymers in Models of Arthritis and Autoimmune Disease

NOTE: The following abbreviations are used for routes of injection: intravenous (iv), intraperitoneal (ip), intramuscular (im), subcutaneous (sc).

The SpA polymers and polymer conjugates are tested for therapeutic efficacy in several well known models of arthritis and autoimmune disease in rodents. These include adjuvant, streptococcal cell wall, *Mycoplasma arthritides* and collagen-induced arthritis (see, for example, Pearson, C. M., *Proc. Soc. Exp. Biol. Med.* 91:95 (1956); Cromartie, W. J. et al., *J Exp. Med* 146:1585 (1977); Trentham, D. E. et al., *J Exp. Med.* 146:857 (1977); Chang, Y. H. et al., *Arthritis Rheum.* 23:62 (1980)).

I. Streptococcal Cell Wall Arthritis Model (See Schwab, J. H. et al., *J Immunol.* 150:4151–4159 (1993))

A. Induction, measurement, and treatment of arthritis

Female Lewis rats weighing about 175g are injected intraarticularly (i.a.) under ether anesthesia above the calcaneus through the Achilles tendon into the tibiotalar (ankle) joint on day 0 with 2.0 μg of rhamnose equivalents (approximately 6.0 μg dry weight) of 100 p peptidoglycan-polysaccharide from cell wall of group A Streptococci (PG-APS) suspended in 10 μl of pyrogen-free saline, as described previously (Esser, R. L., et al., *Arthritis Rheum.* 28:1402 (1985); Stimpson, S. A., et al., In: *Pharmacological Methods in the Control of Inflammation*, J. Chang et al., Eds. Alan R. Liss, Inc., New York, p. 381 (1989)). Right or left joints are injected with PG-APS in alternate animals, and contralateral joints were injected with 10 TI of pyrogen-free saline.

The lateral diameter of the ankle joint is measured with a Fowler Ultra-Cal II digital caliper (Lux Scientific Instrument Corp., New York, N.Y.). The average of three measurements for each joint is recorded. Results are presented as the mean ± SE of the increase in joint diameter (difference between pre- and postreactivation).

B. Histopathology

Rats are sacrificed and the ankle joints are removed, skinned, fixed in formalin, decalcified, embedded in paraffin, sectioned sagitally, and stained with hematoxylin-eosin. The significance of differences between groups is assessed by Student's two tail t-test.

II. Adjuvant Arthritis (AA) Model (See: Chang et al., supra)

Male Lewis rats weighing 235–250 gm are used. Freund's complete adjuvant is either purchased commercially or prepared by grinding powdered *Mycobacterium butyricum* (10 mg; Difco Laboratories) with mineral oil (1.01 ml; Primol 355, Hampden Color Chemical Company). Adjuvant arthritis is produced by a single intradermal injection of the adjuvant into the tail or one hindpaw. The dose is about 0.5 mg heat killed *Mycobacterium tuberculosis* (Mt) suspended in 100 $\mu$l IFA. The volume of the uninjected hindpaw is measured by the method of Winter et al., *Proc. Soc. Exp. Biol. Med.* 111:544 (1962) on day 0 and 16 (with respect to the injection of adjuvant). The increase in the volume of the uninjected hindpaw serves as a measure of arthritis.

To determine the effect of a therapeutic composition, rats are treated with either saline or the composition each day from day -1 to day -15 (with respect to adjuvant injection). The initial paw volume ($V_I$) is measured on the day of adjuvant injection. Sixteen days later, the volume ($V_F$) of the uninjected hindpaw is measured. Percent inhibition is calculated according to the following equation:

$$\%\text{ inhibition} = 1 - \frac{V_F\text{ drug} - V_I\text{ drug}}{V_F\text{ control} - V_I\text{ control}} \times 100$$

Alternatively, severity of arthritis is assessed by scoring each paw from 0 to 4 based on degree of swelling, erythema, and deformity of the joints. Thus the maximum possible arthritis score is 16.

III. Collagen Type II Arthritis (CIA) Model (see Trentham et al., supra)

Sensitization Procedures. Collagen is dissolved in 0.1M acetic acid at a concentration of mg/ml. Equal volumes of collagen solution and CFA or ICFA are mixed and emulsified. One ml of the cold emulsion is immediately injected intradermally in four to six sites on the backs of the rats. Small ulcers frequently form at the injection site, but these heal without sequelae in 7–10 days. Control injections consist of (a) acetic acid emulsified in CFA or ICFA or (b) human or chick type II collagen dissolved in acetic acid and injected intradermally without adjuvant. As an additional control, 1.0 ml of $MgCl_2$-extractable cartilage proteoglycans containing approximately 200 $\mu$g uronate per ml is mixed with 0.5 ml of CFA or ICFA, emulsified, and injected as with collagens. Unless otherwise specified, booster doses consisting of 0.5 mg collagen dissolved in 0.5 ml 0.1 M acetic acid are given ip without adjuvant 21 days after primary immunization. One ml of the $MgCl_2$ extract is given ip after an identical interval to the proteoglycan control animals. Adjuvant arthritis is induced by intradermal injection of 0.1 ml CFA H37 at the base of the tail.

Arthritis Evaluation. Animals are observed daily for the onset of arthritis, and an arthritic index is derived by grading the severity of involvement of each paw from 0 to 4. Scoring is based on the degree of periarticular erythema and edema as well as deformity of the joints (Wood, F. D., el al., *Int. Arch. Allergy Appl. Immunol.* 35:456 (1969)). Swelling of hindpaws is also quantitated by measuring the thickness of the ankle from medial to lateral malleolus with a constant tension caliper (B. C. Ames Co., Waltham, Mass.). Results can be reproducibly expressed to the nearest 0.1 mm.

Histopathology. Animals are sacrificed, and involved paws are amputated on the day of onset of arthritis or at later periods ranging up to 6 mo. after onset. After immersion in 10% neutral formalin, the joints are decalcified, embedded in paraffin, sectioned, and stained with hematoxylin and eosin.

IV. Autoimmune Model MRL/1pr Mice (See: Kim, C. et al., *J. Exp. Med.* 174:1431–1437 (1991))

MRL/Mp-1pr/1pr mice (4–6 wk. old) are purchased from the Jackson Laboratory (Bar Harbor, Me.).

ELISA for Anti-DNA Abs and Circulating Immune Complexes

Polystyrene microtiter wells are coated with double-stranded DNA (ds-DNA) or goat C1 q. Blood obtained from individual mice before the biweekly injections is pooled according to treatment group. Sera are diluted in 0.05% Tween-20 in PBS at a 1:500 dilution and allowed to incubate in the plates for 60 min at room temperature. The plates are then washed three times with PBS-Tween, and 50$\mu$l of 1/1000 dilutions of goat anti-mouse IgG and IgM antibodies conjugated to urease (Sigma Chemical Co.) are added to the plates. After incubation for 30 min., the plates are washed three times with PBS-Tween and twice with 0.15 M NaCl. The plates are then incubated with the urease substrate solution. The urease substrate solution is made according to manufacturer's instructions (Sigma). In short, 8 mg of bromocresol purple is dissolved in 1.48 ml of 0.01M NaOH and then diluted to 100 ml with water. I00mg of urea and 3.7mg of EDTA are dissolved, and the pH is adjusted to 4.8 by the addition of 0.01N NaOH. Colorimetric change is quantified by measuring absorbance at 590 nm using a microplate reader.

Proteinuria and Physical Symptoms

Urine (from at least 4 mice per group) is pooled according to treatment group. Protein concentration and the presence of blood in urine is measured semiquantitatively by commercial reagent strips for urinalysis. Physical symptoms are visually scored as: 0, no symptoms; 0.5, trace; 1–4, when visible symptoms are observed, with 4 being the most severe (physical symptoms include lymphadenomegaly, immune complex vasculitis, and necrosis of the ears). Scores representing physical symptoms are calculated by determining the total score for each group and then dividing by the number of animals alive in that group when the measurement is taken.

For each of the models described above, treatment is started 6–14 days after the injection of the inducing agents (or in the case of MRL mice beginning at 4 weeks of age). Doses vary from 1 ng to 1 $\mu$g of SpA polymers or polymer conjugates and are given iv or ip at 1 week intervals for 4 weeks. Outcomes are assessed as described. For all arthritis models outcome measures include: (a) quantitative measurement and grading of joint swelling erythema or deformity, and (b) assessment of histopathology of joints using a quantitative grading system.

In all the models described, SpA or SpA-SEB polymers at all molecular size ranges tested (covering 64kDa to 10,000 kDa) are effective in significantly reducing measures of arthritis or autoantibodies.

EXAMPLE V

Therapy of Rheumatoid Arthritis in Humans (See: McCarty, D. J., *Arthritis and Allied Conditions*—A Textbook of Rheumatology, 11th ed., Lea & Fibiger, Philadelphia 1989)

Treatment Procedure

Doses of the SpA polymer are determined as described above using, inter alia, appropriate animal models of autoimmune disease. Two classes of therapeutic compositions of two molecular size ranges are administered:

(1) SpA polymers ranging in size from 64 kDa to 1000 kDa, comprising substantially 100% (w/w) polymers;

(2) SpA polymers ranging in size from 1000 kDa to 10,000 kDa, comprising substantially 100% (w/w) polymers;

(3) SpA-SEB polymer conjugates ranging in size from 92 kDa to 1000 kDa, comprising substantially 100% (w/w) polymers; and (4) SpA-SEB polymer conjugates ranging in size from 1000 kDa to 10,000 kDa, comprising substantially 100% (w/w) polymers; and A treatment consists of injecting the patient with 1,100 or 1000 μg SpA polymer or SpA-SEB polymer conjugate intravenously in 200 ml of normal saline over a one hour period twice weekly at three day intervals for six weeks. Clinical responses are assessed by the criteria described below. Treatments are continued in patients with stable or exacerbating disease. Treatment is generally given on an outpatient basis.

CLINICAL OUTCOME MEASURES

Outcome measures used to assess treatment efficacy in RA should detect the smallest clinically important change and, at the same time, be reliable and valid with respect to capturing the dimensionality of the clinical and pathophysiologic responses. To avoid bias, both patients and assessors preferably are blinded during testing.

The methods most commonly used are based on quantitation of cardinal features: pain, swelling, heat and redness. Laboratory tests may also be used in assessment, though a treatment that only reduces a laboratory measure without, for example, relieving joint pain is of less interest. No single ideal method is known to accurately reflect disease activity in arthritis. As a result, it is useful to aggregate end points into a composite index. Composite indices are constructed by statistical or judgmental procedures that allow aggregation of scores assigned to different end points.

Objective and sensitive measurements are preferred to subjective ones. One sensitive parameter to change with antirheumatic drug therapy in RA is the patient's subject assessment of pain relief. Objective measurements include radionuclide joint uptake. Others are the 50-foot walking time and assessment of functional disability (the second most important symptom in osteoarthritis). Examples of useful outcome measures appear in Table 10, below.

Because pain is the major complaint of the rheumatic sufferer, measurement of pain relief is important in assessing clinical response to the therapeutic composition or method of this invention. Adjectival scales may be used with numeric values given to the adjectival scale, for example: 0=no pain, 1=slight pain, 2=moderate pain, 3=severe pain, and 4=extremely severe or agonizing pain. Such a scale is known to discriminate between nonsteroidal anti-inflammatory analgesics and placebo in short-term trials (Lee, P., *J Rheumatol.* 3:283–294 (1976)). Other methods of measuring pain include assessment of pain threshold and pain tolerance (Huskisson, E. C., *Clin. Rheum. Dis.* 2:37–49 (1976)).

TABLE 10

Outcome Measures for Clinical Trials in Arthritis
Altman, R.D. et al., Clin. Rheum. Dis. 9:681–693 (1983)

| FDA Guidelines (1977) | Bellamy and Buchanan |
|---|---|
| Joint swelling | Clin. Rheumatol. 3:293–305 (1984) |
| Joint redness | Pain |
| Tenderness on pressure | Patient global assessment |
| Pain at rest or on motion | Range of movement |
| Range of motion | Physician global assessment |
| 50-foot walking time | Joint stiffness |
| Clinician's global assessment | Qualitative aspects of sleep |
| Patient's global assessment | Walking time |
| Altman et al. (supra) | Activities of daily living |
| Pain (using visual analogue scales) | Joint tenderness |
| Tenderness on pressure/motion | Analgesic compound |
| Clinician's global assessment of current status and | Joint swelling |
| degree of change in status | Signal joints |
| Patient's global assessment of current status and | Ascent time |
| degree of change in status | Muscle power |
| 50-foot walking time (for patients with hip and/or | Hand function |
| knee involvement) | Radiology |
| Grip strength (for patients with hand involvement) | Joint temperature |

To score joint tenderness, firm digital pressure is applied to the joint margins and the degree of tenderness is graded by the patient's response. Lansbury's Articular Index (Lansbury, J., *Arthritis Rheum.* 1:505–522 (1958)) is useful in assessing progress. A simple count of clinically active joints, as determined by pain on passive motion, tenderness on pressure, or inflammatory joint swelling is used (Cooperat. Clin. Comm. Amer. Rheum. Assoc., *Clin. Phar-*

*macol. Ther.* 8:11–38 (1967)). Scoring a few selected "signal" joints may permit better assessment of therapeutic effect than a total joint count. A standardized dolorimeter tested against the Lansbury indices is highly reproducible. The Ritchie Articular Index (RAI) is based on summation of joint responses after firm digital pressure. The responses are recorded as 0=no tenderness, +1= patient says it is tender, +2= patient says it is tender and winces, and +3= patient says it is tender, winces, and withdraws limb. The sum of this Index is 78 and reflects exacerbations of disease and improvement induced by antirheumatic drugs. This index correlates with the patient's assessment of pain, in the upper limbs with grip strength, and in the lower limbs with the time to walk 50 feet.

Various instruments are available to measure grip strength which is determined by the strength of the muscles in the forearm and hand, and the pain and degree of joint destruction in the wrist, hand, and finger joints; grip strength correlates with the RAI.

The range of motion of peripheral joints in normal subjects is known, and these measures have been assessed in studies of ankylosing spondylitis. Spinal movement is measured by several methods including the Dunham spondylometer (Hart, F. D. et al., *Ann. Rheum. Dis.* 14:77–89 (1955); Anderson, J. A. D., *Clin. Rheum. Dis.* 8:631–653 (1982)), skin distraction (Moll, J. M. H. et al., *Rheum. Phys. Med.* 11:293–312 (1972)), an inclinometer (Domjan, L. et al., *Hung. Rheum.,* 28(Suppl.):71–76 (1987)).

Timing of certain movements or set maneuvers related to activities of daily living, are useful, in particular the time to walk 50 feet (Lee, supra; Grace, E. M. et al., *Br. J Rheumatol.* 27:372–374 (1988)).

Increase in warmth of overlying skin is a cardinal feature of inflammation and can be measured in various ways (Bacon, P. A. et al, *Clin. Rheum. Dis.* 2: 51–65 (1976)). Infrared quantitative thermography shows reproducible changes in disease activity and is useful in assessing efficacy of a treatment composition or method (Ingpen, M. L., *Ann. Phys. Med.* 9:322–327 (1968)). Thermography provides a noninvasive, reproducible, sensitive, and quantifiable method of assessing improvement in joint inflammation.

LABORATORY TESTS

Certain laboratory tests reflect the severity of joint inflammation and may be used to monitor the efficacy of the therapeutic compositions and methods of this invention. The most frequently used test is the erythrocyte sedimentation rate (ESR). Other measures used include evaluation of various acute-phase reactants, such as C-reactive protein haptoglobin, fibrinogen, β-2 macroglobulin, and plasma viscosity (McConkey, B. et al., *Q.J. Med, New Series* 41:115–125 (1972);

McConkey, B. et al., *Q.J Med., New Series* 42:785–791 (1973); Constable, T. J. et al., Lancet 1:1176–1179 (1975); Crook, L. et al., *Ann. Clin. Lab. Sci.* 10:368–376 (1980); Dixon, J. A. et al., *Scand. J. Rheumatol.* 13:39–44 (1984); Cockel, R. et al., *Ann. Rheum. Dis.* 30:166–170 (1971)); titer of IgM rheumatoid factor or of immune complexes (Pope, R. M. et al., *Ann. Rheum. Dis.* 45:183–189 (1986); Reeback J. S. et al, *Ann. Rheum. Dis.* 44:79–82 (1986); Reynolds, W. J. et al., *J Rheumatol.* 13:700–706 (1986)); tests of lymphocyte function (Reynolds, W. J. et al., *J Rheumatol.* 13:700–706 (1986); Alepa, F. P. et al., *Arthritis Rheum.* 13:754–760 (1970); Swanson, M. A. et al., *N. Engl. J Med.* 277:163–170 (1967)); displacement of L-tryptophan from serum albumin; serum iron concentration (Cockel, supra), eosinophilia, thrombocytosis (Hutchinson, R. M. et al., *Ann. Rheum. Dis.* 35:138–142 (1976)); serum concentrations of sulfhydryl groups (Lorber, A. et al., *Metabolism* 20:446–455 (1971)); serum copper concentrations (Brown, D. H. et al., *Ann. Rheum. Dis.* 38:174–176 (1979)); serum propeptide levels (Horsley-Petersen et al., *Rheum.* 29:592–599 (1986)); synovial fluid analysis (Hall, S. H. et al., *Ann. Rheum. Dis.* 37:351–356 (1978)).

Various methods are used to score radiologic changes in rheumatoid arthritis, the most useful of which are count erosions and assessment of joint space narrowing. Radionuclides are used to quantify joint inflammation (Dick, W. C., *Semin. Arthritis Rheum.* 1:301–325 (1972); Dick, W. C. et al., *Clin. Rheum. Dis.* 2:67–76 (1976); Wallace, D. J. et al., *Arthritis Rheum.* 11:172–176 (1981)). These are administered intra-articularly and the rate of clearance from the joint determined or, alternatively, they are administered iv and the rate of accumulation over a joint (or joints) measured. The clearance of $^{133}$Xe after intra-articular injection provides an indirect measurement of synovial blood flow. $^{99m}TcO_4$ is also used. Radionuclide joint uptake in both large and small joints is reduced with successful anti-rheumatic therapeutics such as NSAIDs, corticosteroids, gold or D-penicillamine.

RESULTS

Three hundred patients with RA are treated. According to the 8 measures listed under "FDA Guidelines" in Table 10, above, greater than 80% of the treated patients show significant cumulative improvement across all measures.

Toxicity

The incidence of side effects (as % of total treatments) are as follows: chills - 10; fever - 10; pain - 5; nausea - 5; respiratory - 3; headache - 3; tachycardia - 2; vomiting - 2; hypertension - 2; hypotension - 2; joint pain - 2; rash - 2; flushing - 1; diarrhea - 1; itching/hives - 1; bloody nose - 1; dizziness - <1; cramps - <1; fatigue - <1; feeling faint - <1; twitching - <1; blurred vision - <1; gastritis<1; redness on hand - <1. Fever and chills are the most common side effects observed. Side effects are somewhat less frequent in patients treated with SpA polymers compared with SpA-SEB polymers. Side effects are less prevalent with the 1 μg and 100 μg SpA-SEB polymer infusions but this is not statistically different from the group receiving 1000 μg infusions. Other minor changes observed are clinically insignificant.

EXAMPLE VI

Antitumor Effects of SpA Polymers in Animal Models of Human Tumors

The SpA polymers and polymer conjugates are tested for therapeutic efficacy in several well established rodent models which are considered to be highly representative of a broad spectrum of human tumors. These approaches are described in detail in Geran, R. I. et al., "Protocols for Screening Chemical Agents and Natural Products Against Animal Tumors and Other Biological Systems (Third Edition)", *Canc. Chemother. Reports*, Part 3, 3:1–112, which is hereby incorporated by reference in its entirety.

I. GENERAL TEST EVALUATION PROCEDURES

A. Calculation of Mean Survival Time Mean survival time is calculated according to the following formula:

$$\text{Mean survival time (days)} = \frac{\Sigma S + AS_{(A-1)} - (B+1)NT}{S_{(A-1)} - NT}$$

Definitions: Day: Day on which deaths are no longer considered due to drug toxicity. Example: with treatment starting on Day I for survival systems (such as L1210, P388, B16, 3LL, and W256): Day A: Day 6. Day B: Day beyond which control group survivors are considered "no-takes." Example: with treatment starting on Day 1 for survival systems (such as L1210, P388, and W256), Day B–Day 18. For B16, transplanted AKR, and 3LL survival systems, Day B is to be established. ΣS: If there are "no-takes" in the treated group, ΣS is the sum from Day A through Day B. If there are no "no-takes" in the treated group, ΣS is the sum of daily survivors from Day A onward. $S_{(A-1)}$: Number of survivors at the end of Day (A-1). NT: Number of "no-takes".

B. T/C Computed for all treated groups

T/C is the ratio (expressed as a percent) of the mean survival time of the treated group divided by the mean survival time of the control group. Treated group animals surviving beyond Day B, according to the chart below, are eliminated from calculations:

| No of survivors in treated group beyond Day B | Percent of "no-takes" in control group | Conclusion |
| --- | --- | --- |
| 1 | Any percent | "no-take" |
| 2 | <10 | drug inhibition |
| | $^3$10 | "no-takes" |
| $^3$3 | <15 | drug inhibitions |
| | $^3$15 | "no-takes" |

Positive control compounds are not considered to have "no-takes" regardless of the number of "no-takes" in the control group. Thus, all survivors on Day B are used in the calculation of T/C for the positive control. Surviving animals are evaluated and recorded on the day of evaluation as "cures" or "no-takes."

Calculation of Median Survival Time

Median Survival Time is defined as the median day of death for a test or control group. If deaths are arranged in chronological order of occurrence (assigning to survivors, on the final day of observation, a "day of death" equal to that day), the median day of death is a day selected so that one half of the animals died earlier and the other half died later or survived. If the total number of animals is odd, the median day of death is the day that the middle animal in the chronological arrangement died. If the total number of animals is even, the median is the arithmetical mean of the two middle values. Median survival time is computed on the basis of the entire population and there are no deletion of early deaths or survivors, with the following exception:

C. Computation of Median Survival Time From Survivors

If the total number of animals including survivors (N) is even, the median survival time (days) (X+Y)/2, where X is the earlier day when the number of survivors is ≲ N/2, and Y is the earliest day when the number of survivors ≲ (N/2)-1. If N is odd, the median survival time (days) is X.

D. Computation of Median Survival Time From Mortality Distribution If the total number of animals including survivors (N) is even, the median survival time (days) (X+Y)/2, where X is the earliest day when the cumulative number of deaths is ≳ N/2, and Y is the earliest day when the cumulative number of deaths is$^3$ (N/2)+1. If N is odd, the median survival time (days) is X. Cures and "No-Takes": "Cures" and "no-takes" in systems evaluated by median survival time are based upon the day of evaluation. On the day of evaluation any survivor not considered a "no-take" is recorded as a "cure." Survivors on day of evaluation are recorded as "cures" or "no-takes," but not eliminated from the calculation of the median survival time. E. Calculation of Approximate Tumor Weight From Measurement of Tumor Diameters with Vernier Calipers The use of diameter measurements (with Vernier calipers) for estimating treatment effectiveness on local tumor size permits retention of the animals for lifespan observations. When the tumor is implanted sc, tumor weight is estimated from tumor diameter measurements as follows. The resultant local tumor is considered a prolate ellipsoid with one long axis and two short axes. The two short axes are assumed to be equal. The longest diameter (length) and the shortest diameter (width) are measured with Vernier calipers. Assuming specific gravity is approximately 1.0, and II is about 3, the mass (in mg) is calculated by multiplying the length of the tumor by the width squared and dividing the product by two.

$$\text{Tumor weight (mg)} = \frac{\text{length (mm)} \times (\text{width [mm]})^2}{2} \text{ or } \frac{L \times (W)^2}{2}$$

The reporting of tumor weights calculated in this way is acceptable inasmuch as the assumptions result in as much accuracy as the experimental method warrants.

F. Calculation of Tumor Diameters

The effects of a drug on the local tumor diameter may be reported directly as tumor diameters without conversion to tumor weight. To assess tumor inhibition by comparing the tumor diameters of treated animals with the tumor diameters of control animals, the three diameters of a tumor are averaged (the long axis and the two short axes). A tumor diameter T/C of 75% or less indicates activity and a T/C of 75% is approximately equivalent to a tumor weight T/C of 42%.

G. Calculation of Mean Tumor Weight From Individual Excised Tumors

The mean tumor weight is defined as the sum of the weights of individual excised tumors divided by the number of tumors. This calculation is modified according to the rules listed below regarding "no-takes." Small tumors weighing 39 mg or less in control mice or 99 mg or less in control rats, are regarded as "no-takes" and eliminated from the computations. In treated groups, such tumors are defined as "no-takes" or as true drug inhibitions according to the following rules:

| Percent of small tumors in treated group | Percent of "no-takes" in control group | Action |
| --- | --- | --- |
| ≦17 | Any percent | no-take; not used in calculations |
| 18–39 | <10 | drug inhibition; use in calculations |
| | ≧10 | no-takes; not used in calculations |

-continued

| Percent of small tumors in treated group | Percent of "no-takes" in control group | Action |
|---|---|---|
| ≧40 | <15 | drug inhibition; use in calculations |
| | ≧15 | Code all nontoxic tests "33" |

Positive control compounds are not considered to have "no-takes" regardless of the number of "no-takes" in the control group. Thus, the tumor weights of all surviving animals are used in the calculation of T/C for the positive control. T/C are computed for all treated groups having more than 65% survivors.

The T/C is the ratio (expressed as a percent) of the mean tumor weight for treated animals divided by the mean tumor weight for control animals. SDs of the mean control tumor weight are computed the factors in a table designed to estimate SD using the estimating factor for SD given the range (difference between highest and lowest observation). *Biometrik Tables for Statisticians* (Pearson E S, and Hartley H G, eds.) Cambridge Press, vol. 1, table 22, p. 165.

II. SPECIFIC TUMOR MODELS

A. Lymphoid Leukemia L1210

Summary: Ascitic fluid from donor mouse is transferred into recipient $BDF_1$ or $CDF_1$ mice. Treatment begins 24 hours after implant. Results are expressed as a percentage of control survival time. Under normal conditions, the inoculum site for primary testing ip or iv, and the parameter is mean survival time. Origin of tumor line: induced in 1948 in spleen and lymph nodes of mice by painting skin with MCA. *J Natl Cancer Inst.* 13:1328, 1953.

Animals Propagation: DBA/2 mice (or $BDF_1$ or $CDF_1$ for one generation). Testing: $BDF_1$ (C57BL/6×DBA/2) or $CDF_1$ (BALB/c×DBA/2) mice. Weight: Within a 3-g weight range, with a minimum weight of 18g for males and 17g for females. One sex used for all test and control animals in one experiment. Experiment Size: Six animals per test group. Control Groups: Number of animals varies according to number of test groups.

Tumor Transfer Inject ip, 0.1 ml of diluted ascitic fluid containing $10^5$ cells. Time of Transfer for Propagation: Day 6 or 7. Time of Transfer for Testing: Day 6 or 7.

Testing Schedule Day 0: Implant tumor. Prepare materials. Run positive control in every odd-numbered experiment. Record survivors daily. Day 1: Weigh and randomize animals. Begin treatment with therapeutic composition. The therapeutic compositions tested are discussed more fully in Section G, below. Any surviving mice are sacrificed after 4 weeks of therapy. Day 5: Weigh animals and record. Day 20: If there are no survivors except those treated with positive control compound, evaluate study. Day 30: Kill all survivors and evaluate experiment.

Quality Control Acceptable control survival time is 8–10 days. Positive control compound is 5-fluorouracil; single dose is 200 mg/kg/injection, intermittent dose is 60 mg/kg/injection, and chronic dose is 20 mg/kg/injection. Ratio of tumor to control (T/C) lower limit for positive control compound is [3] 135%

Evaluation

Compute mean animal weight on Days 1 and 5, and at the completion of testing compute T/C for all test groups with >65% survivors on Day 5. A T/C value ≲ 85% indicates a toxic test. An initial T/C ≳ 125% is considered necessary to demonstrate activity. A reproduced T/C ≳ 125% is considered worthy of further study. For confirmed activity a composition should have two multi-dose assays that produce a T/C ≳125%.

B. Lymphocytic Leukemia P388 Summary: Ascitic fluid from donor mouse is implanted in recipient $BDF_1$ or $CDF_1$ mice. Treatment begins 24 hours after implant. Results are expressed as a percentage of control survival time. Under normal conditions, the inoculum site for primary screening is ip, the SpA polymeric composition is administered ip or iv at intervals of 1, 3 or 7 days per week. The parameter is median survival time. Origin of tumor line: induced in 1955 in a DBA/2 mouse by painting with MCA. *Scientific Proceedings, Pathologists and Bacteriologists* 33:603, 1957.

Animals

Propagation: DBA/2 mice (or $BDF_1$ or $CDF_1$ for one generation) Testing: $BDF_1$ (C57BL/6×DBA/2) or $CDF_1$ (BALB/c×DBA/2) mice. Weight: Within a 3-g weight range, with a minimum weight of 18 g for males and 17 g for females One sex used for all test and control animals in one experiment. Experiment Size: Six animals per test group. Control Groups: Number of animals varies according to number of test groups.

Tumor Transfer Implant: Inject ip; Size of Implant: 0.1 ml diluted ascitic fluid containing 106 cells. Time of Transfer for Propagation: Day 7. Time of Transfer for Testing: Day 6 or 7.

Testing Schedule

Day 0: Implant tumor. Prepare materials. Run positive control in every odd-numbered experiment. Record survivors daily. Day 1: Weigh and randomize animals. Begin treatment with therapeutic composition. See Section G, below, for a fuller discussion of therapeutic compositions and treatment regimen. Any surviving mice are sacrificed after 4 weeks of therapy. Day 5: Weigh animals and record. Day 20: If there are no survivors except those treated with positive control compound, evaluate experiment. Day 30: Kill all survivors and evaluate experiment.

Quality Control

Acceptable median survival time is 9–14 days. Positive control compound is 5-fluorouracil: single dose is 200 mg/kg/injection, intermittent dose is 60 mg/kg/injection, and chronic dose is 20 mg/kg/injection. T/C lower limit for positive control compound is ≳ 135% Check control deaths, no takes, etc.

Evaluation

Compute mean animal weight on Days 1 and 5, and at the completion of testing compute T/C for all test groups with >65% survivors on Day 5. A T/C value ≲ 85% indicates a toxic test. An initial T/C ≳125% is considered necessary to demonstrate activity. A reproduced T/C≳125% is considered worthy of further study. For confirmed activity a synthetic must have two multi-dose assays (each performed at a different laboratory) that produce a T/C ≳ 125%; a natural product must have two different samples that produce a T/C ≳ 125% in multi-dose assays.

C. Melanotic Melanoma B16

Summary: Tumor homogenate is implanted ip or sc in $BDF_1$ mice. Treatment begins 24 hours after either ip or sc implant or is delayed until an sc tumor of specified size (usually approximately 400 mg) can be palpated. Results expressed as a percentage of control survival time. The SpA polymeric composition is administered ip or iv, and the parameter is mean survival time. Origin of tumor line: arose spontaneously in 1954 on the skin at the base of the ear in a C57BL/6 mouse *Handbook on Genetically Standardized Jax Mice*. Roscoe B. Jackson Memorial Laboratory, Bar Harbor, Me., 1962. See also *Ann NY AcadSci* 100, *Parts* 1 and 2, 1963.

Animals

Propagation: C57BL/6 mice. Testing: $BDF_1$ (C57BL/6×DBA/2) mice. Weight: Within a 3-g weight range, with a minimum weight of 18g for males and 17g for females. One sex used for all test and control animals in one experiment. Experiment Size: Ten animals per test group. For control groups, the number of animals varies according to number of test groups.

Tumor Transfer

Propagation: Implant fragment sc by trochar or 12-gauge needle or tumor homogenate (see below) every 10–14 days into axillary region with puncture in inguinal region. Testing: Excise sc tumor on Day 10–14. Homogenate: Mix 1 g or tumor with 10 ml of cold balanced salt solution and homogenize, and implant 0.5 ml of this tumor homogenate ip or sc. Fragment: A 25-mg fragment may be implanted sc.

Testing Schedule

Day 0: Implant tumor. Prepare materials. Run positive control in every odd-numbered experiment. Record survivors daily. Day 1: Weigh and randomize animals. Begin treatment with therapeutic composition. See Section G, below, for a fuller discussion of therapeutic compositions and treatment regimen. Any surviving mice are sacrificed 8 weeks of therapy. Day 5: Weigh animals and record. Day 60: Kill all survivors and evaluate experiment.

Quality Control

Acceptable control survival time is 14–22 days. Positive control compound is 5-fluorouracil: single dose is 200 mg/kg/injection, intermittent dose is 60 mg/kg/injection, and chronic dose is 20 mg/kg/injection. T/C lower limit for positive control compound is ≳ 135% Check control deaths, no takes, etc.

Evaluation

Compute mean animal weight on Days 1 and 5, and at the completion of testing compute T/C for all test groups with >65% survivors on Day 5. A T/C value ≤85% indicates a toxic test. An initial T/C ≳125% is considered necessary to demonstrate activity. A reproduced T/C ≳ 125% is considered worthy of further study. For confirmed activity a therapeutic composition should have two multi-dose assays that produce a T/C ≳ 125%.

Metastasis after IV Injection of Tumor Cells $10^5$ B16 melanoma cells in 0.3 ml saline are injected intravenously in C57BL/6 mice. The mice are treated intravenously with the therapeutic composition Controls receive saline. The treatment is given as one dose per week. Mice sacrificed after 4 weeks of therapy, the lungs are removed and metastases are enumerated.

C. 3LL Lewis Lung Carcinoma

Summary: Tumor may be implanted sc as a 2–4 mm fragment, or im as a $2\times10^6$-cell inoculum. Treatment begins 24 hours after implant or is delayed until a tumor of specified size (usually approximately 400 mg) can be palpated. The SpA polymeric composition is administered ip daily for 11 days and the results are expressed as a percentage of the control. Origin of tumor line: arose spontaneously in 1951 as carcinoma of the lung in a C57BL/6 mouse. Cancer Res 15:39, 1955. See, also Malave, I. et al., *J Nat'l. Canc. Inst.* 62:83–88 (1979).

Animals

Propagation: C57BL/6 mice. P Testing: $BDF_1$ mice or C3H. Weight: Within a 3-g weight range, with a minimum weight of 18 g for males and 17 g for females. One sex used for all test and control animals in one experiment. Experiment Size: Six animals per test group for sc implant, or ten for im implant. For control groups, the number of animals varies according to number of test groups.

Tumor Transfer

Implant: Inject cells im in hind leg or implant fragment sc in axillary region with puncture in inguinal region. Time of Transfer for Propagation: Days 12–14. Time of Transfer for Testing: Days 12–14.

Testing Schedule

Day 0: Implant tumor. Prepare materials. Run positive control in every odd-numbered experiment. Record survivors daily. Day 1: Weigh and randomize animals. Begin treatment with therapeutic composition. See Section G, below, for a fuller discussion of therapeutic compositions and treatment regimen. Any surviving mice are sacrificed after 4 weeks of therapy. Day 5: Weigh animals and record. Final Day: Kill all survivors and evaluate experiment.

Quality Control

Acceptable im tumor weight on Day 12 is 500–2500 mg. Acceptable im tumor median survival time is 18–28 days. Positive control compound is cyclophosphamide: 20 mg/kg/injection, qd, Days 1–11. Check control deaths, no takes, etc.

Evaluation Compute mean animal weight when appropriate, and at the completion of testing compute T/C for all test groups. When the parameter is tumor weight, a reproducible T/C ≲ 42% (reduction in weight) is considered necessary to demonstrate activity. When the parameter is survival time, a reproducible T/C ≳ 125% is considered necessary to demonstrate activity. For confirmed activity a synthetic must have two multi-dose assays (each performed at a different laboratory); a natural product must have two different samples.

D. 3LL Lewis Lung Carcinoma Metastasis Model

This model has been utilized by a number of investigators. See, for example, Gorelik, E. et al., *J Nat'l. Canc. Inst.* 65:1257–1264 (1980); Gorelik, E. et al., *Rec. Results Canc. Res.* 75:20–28 (1980); Isakov, N. et al., *Invasion Metas.* 2:12–32 (1982); Talmadge J. E. et al., *J Nat'l. Canc. Inst.* 69:975–980 (1982); Hilgard, P. et al., *Br. J. Cancer* 35:78–86(1977)). Mice are male C57BL/6 mice, 2–3 months old.

Tumor: The 3LL Lewis Lung Carcinoma is maintained by sc transfers in C57BL/6 mice. Following sc, im or intrafoot pad transplantation, this tumor produces metastases, preferentially in the lungs. Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95–99% (by trypan blue dye exclusion). Viable tumor cells ($3\times10^4$-$5\times10^6$) ) suspended in 0.05 ml PBS are injected into the right hind foot pads of C57BL/6 mice. The day of tumor appearance and the diameters of established tumors are measured by caliper every two days.

See Section G, below, for a fuller discussion of therapeutic compositions and treatment regimen. The treatment is given as one or two doses per week.

In experiments involving tumor excision, mice with tumors 8–10 mm in diameter are divided into two groups. In one group, legs with tumors are amputated after ligation above the knee joints. Mice in the second group are left intact as nonamputated tumor-bearing controls. Amputation of a tumor-free leg in a tumor-bearing mouse has no known effect on subsequent metastasis, ruling out possible effects of anesthesia, stress or surgery. Surgery is performed under Nembutal anesthesia (60 mg veterinary Nembutal per kg body weight).

Determination of Metastasis Spread and Growth

Mice are killed 10–14 days after amputation. Lungs are removed and weighed. Lungs are fixed in Bouin's solution and the number of visible metastases is recorded. The diameters of the metastases are also measured using a binocular stereoscope equipped with a micrometer-containing ocular under 8X magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur, M. L. et al., *J Lab. Clin. Med.* 89:217–228 (1977). Ten days following tumor amputation, 25 $\mu$g of fluorodeoxyuridine is inoculated into the peritoneums of tumor-bearing (and, if used, tumor-resected mice. After 30 min, mice are given 1 $\mu$Ci of $^{125}$IdUrd (iododeoxyuridine). One day later, lungs and spleens are removed and weighed, and a degree of $^{125}$IdUrd incorporation is measured using a gamma counter.

Statistics: Values representing the incidence of metastases and their growth in the lungs of tumor-bearing mice are not normally distributed. Therefore, non-parametric statistics such as the Mann-Whitney U-Test may be used for analysis.

Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of large doses of 3LL cells ($1–5\times10^6$) followed by surgical removal, the number of metastases was lower than that in nonoperated tumor-bearing mice, though the volume of metastases was higher than in the nonoperated controls.

Using $^{125}$IdUrd incorporation as a measure of lung metastasis, no significant differences were found between the lungs of tumor-excised mice and tumor-bearing mice originally inoculated with $1\times10^6$ 3LL cells. Amputation of tumors produced following inoculation of $1\times10^5$ tumor cells dramatically accelerated metastatic growth. These results were in accord with the survival of mice after excision of local tumors. The phenomenon of acceleration of metastatic growth following excision of local tumors had been observed by other investigators. The growth rate and incidence of pulmonary metastasis were highest in mice inoculated with the lowest doses ($3\times10^4$-$1\times10^5$) of tumor cells and characterized by the longest latency periods before local tumor appearance. Immunosuppression accelerated metastatic growth, though nonimmunologic mechanisms participate in the control exerted by the local tumor on lung metastasis development. These observations have implications for the prognosis of patients who undergo cancer surgery.

E. Walker Carcinosarcoma 256

Summary: Tumor may be implanted sc in the axillary region as a 2–6 mm fragment, im in the thigh as a 0.2-ml inoculum of tumor homogenate containing $10^6$ viable cells, or ip as a 0.1 -ml suspension containing $10^6$ viable cells. SpA polymeric composition treatment is usually ip. Origin of tumor line: arose spontaneously in 1928 in the region of the mammary gland of a pregnant albino rat. *J Natl Cancer Inst* 13:1356, 1953.

Animals Propagation: Random-bred albino Sprague-Dawley rats. Testing: Fischer 344 rats or random-bred albino rats. Weight Range: 50–70 g (maximum of 10-g weight range within each experiment). Sex: One sex used for all test and control animals in one experiment. Experiment Size: Six animals per test group. For control groups, the number of animals varies according to number of test groups.

Time of Tumor Transfer Time of Transfer for Propagation: Day 7 for im or ip implant; Days 11–13 for sc implant.

Time of Transfer for Testing: Day 7 for im or ip implant; Days 11–13 for sc implant.

Tumor Transfer Sc fragment implant is by trochar or 12-gauge needle into axillary region with puncture in inguinal area. Im implant is with 0.2 ml of tumor homogenate (containing $10^6$ viable cells) into the thigh. Ip implant is with 0.1 ml of suspension (containing $10^6$ viable cells) into the ip cavity.

Testing Schedule Prepare and administer SpA polymeric compositions on days 1–9. Weigh animals on days 1 and 5 and evaluate on day 30. Day 0: Implant tumor. Run positive control in every odd-numbered experiment. Record survivors daily. Day 1: Weigh and randomize animals. Begin treatment. See Section G, below, for a fuller discussion of therapeutic compositions and treatment regimen. Final Day: Kill all survivors and evaluate experiment.

Quality Control Acceptable im tumor weight or survival time: 3–12 g. or 5WA21: 5–9 days.

Evaluation Compute mean animal weight when appropriate, and at the completion of testing compute T/C for all test groups. When the parameter is tumor weight, a reproducible T/C $\leq$ 42% is considered necessary to demonstrate activity. When the parameter is survival time, a reproducible T/C $\geq$ 125% is considered necessary to demonstrate activity. For confirmed activity a therapeutic agent must have activity in two multi-dose assays.

F. A20 lymphoma $10^6$ murine A20 lymphoma cells in 0.3 ml saline are injected sc in Balb/c mice. The mice are treated intravenously with SpA polymers or polymer conjugates. See Section G, below, for a fuller discussion of therapeutic compositions and treatment regimen. The treatment is given as one dose per week. Tumor growth is monitored daily by physical measurement of tumor size and calculation of total tumor volume. After 4 weeks of therapy the mice are sacrificed.

G. Treatment Regimen and Results

For determining efficacy in the tumor models described above, two classes of therapeutic compositions, in two molecular size ranges, are initially administered:

(1) SpA polymers ranging in size from 64 kDa to 1000 kDa, comprising substantially >50% (w/w) polymers;

(2) SpA polymers ranging in size from 1000 kDa to 10,000 kDa, comprising substantially >50% (w/w) polymers;

(3) SpA-SEB polymer conjugates ranging in size from 92 kDa to 1000 kDa, comprising substantially >50% (w/w) polymers; and (4) SpA-SEB polymer conjugates ranging in size from 1000 kDa to 10,000 kDa, comprising substantially >50% (w/w) polymers.

Treatment consists of injecting animals iv or ip with 1, 100 or 1000 ng SpA polymer or SpA-SEB polymer conjugate in 0.1–0.5 ml of normal saline. Unless indicated otherwise above, treatments are 1 or 3 times per week for the duration of the trial as described for each tumor model.

The results shown in Table 11 are for each composition and dose tested and are statistically significant by the appropriate statistical test.

TABLE 11

| Tumor Model | Parameter | % of Control Response |
|---|---|---|
| L1210 | Mean survival time | >130% |
| P388 | Median survival time | >130% |
| B16 | Mean survival time | >130% |
| B16 metastasis | Median number of metastases | <70% |
| 3LL | Mean survival time | >130% |
| | Mean tumor weight | <40% |
| 3LL metastasis | Median survival time | >130% |
| | Mean lung weight | <60% |
| | Median number of metastases | <60% |
| | Median volume of metastases | <60% |
| | Median volume of metastases | <60% |
| | Median uptake of IdUrd | <60% |
| Walker carcinoma | Median survival time | >130% |
| | Mean tumor weight | <40% |
| A20 | Mean survival time | >130% |
| | Mean tumor volume | <40% |

Additional tumor models of carcinoma and sarcoma originating from various primary sites and prepared as established tumors at primary and/or metastatic sites will be utilized to test further the efficacy of the SpA polymers.

EXAMPLE VII

Anti Tumor Effects of Infused SpA Polymers in Humans Patients

All patients treated have histologically confirmed malignant disease including carcinomas, sarcomas, melanomas, lymphomas and leukemia. and have failed conventional therapy. Patients may be diagnosed as having any stage of metastatic disease involving any organ system. Staging describes both tumor and host, including organ of origin of the tumor, histologic type, histologic grade, extent of tumor size, site of metastases and functional status of the patient. A general classification includes the known ranges of Stage 1 (localized disease) to Stage 4 (widespread metastases). Patient history is obtained and physical examination performed along with conventional tests of cardiovascular and pulmonary function and appropriate radiologic procedures. Histopathology is obtained to verify malignant disease.

Treatment Procedure

Doses of the SpA polymer are determined as described above using, inter alia, appropriate animal models of tumors. Two classes of therapeutic compositions in two molecular size ranges are administered:

(1) SpA polymers ranging in size from 64 kDa to 1000 kDa, comprising substantially 100% (w/w) polymers;

(2) SpA polymers ranging in size from 1000 kDa to 10,000 kDa, comprising substantially 100% (w/w) polymers;

(3) SpA-SEB polymer conjugates ranging in size from 92 kDa to 1000 kDa, comprising substantially 100% (w/w) polymers; and (4) SpA-SEB polymer conjugates ranging in size from 1000 kDa to 10,000 kDa, comprising substantially 100% (w/w) polymers; and A treatment consists of injecting the patient with 1, 100 or 1000 $\mu$g SpA polymer or SpA-SEB polymer conjugate intravenously in 200 ml of normal saline over a one hour period. Treatments are given 3×/week for a total of 12 treatments. Patients with stable or regressing disease are treated beyond the 12th treatment. Treatment is given on either an outpatient or inpatient basis as needed.

Patient Evaluation

Assessment of response of the tumor to the therapy is made once per week during therapy and 30 days thereafter. Depending on the response to treatment, side effects, and the health status of the patient, treatment is terminated or prolonged from the standard protocol given above. Tumor response criteria are those established by the International Union Against Cancer and are listed below.

| RESPONSE | DEFINITION |
|---|---|
| Complete remission (CR) | Disappearance of all evidence of disease |
| Partial remission (PR) | ≧50% decrease in the product of the two greatest perpendicular tumor diameters; no new lesions |
| Less than partial remission (<PR) | 25%–50% decrease in tumor size, stable for at least 1 month |
| Stable disease | <25% reduction in tumor size; no progression or new lesions |
| Progression | ≧25% increase in size of any one measured lesion or appearance of new lesions despite stabilization or remission of disease in other measured sites |

The efficacy of the therapy in a patient population is evaluated using conventional statistical methods, including, for example, the Chi Square test or Fisher's exact test. Long-term changes in and short term changes in measurements can be evaluated separately.

Results

One hundred and fifty patients are treated. The results are summarized in Table 12. Positive tumor responses are observed in 80% of the patients as follows:

TABLE 12

| All Patients | Response | No. | % |
|---|---|---|---|
| | PR | 10 | 66% |
| | <PR | 20 | 33% |

| By Tumor Type: | Response | % of Patients |
|---|---|---|
| Breast adenocarcinoma | PR + <PR | 80% |
| Gastrointestinal carcinoma | PR + <PR | 75% |
| Lung Carcinoma | PR + <PR | 75% |
| Prostate Carcinoma | PR + <PR | 75% |
| Lymphoma/Leukemia | PR + <PR | 75% |
| Head and Neck Cancer | PR + <PR | 75% |

TABLE 12-continued

| | | |
|---|---|---|
| Renal and Bladder Cancer | PR + <PR | 75% |
| Melanoma | PR + <PR | 75% |

Toxicity

Toxicity is essentially the same as that observed in the RA patients described in Example V above.

DISCUSSION OF EXAMPLES

According to criteria set forth by Parikh et al., *Meth. Enzymol.* 4:77 (1974) and Wilchek et al., *Meth. Enzymol.* 104:3 (1984), the presence in a perfusate of SpA from a SpA-silica column after perfusion with plasma, protease-free human albumin, acid-water, 6M guanidine HCl and $Na_2CO_3$ strongly indicates that non-covalently bound bacterial products were associated with the column. When a Prosorba® column was "washed" exactly as described by Balint et al. (supra) using only acid water, pH 2.25, additional non-covalently bound SpA was found to elute. Hence, the initial acid wash used in column preparation did not remove all non-covalently bound material from the silica matrix. In fact, additional acid-labile SpA readily desorbed upon further perfusion with acid water. These results confirm that the Prosorba® column, in effect, performs as an ion exchanger, readily releasing non-covalently bound SpA when a "displacing" protein, such as HSA is perfused through it.

Moreover, the present inventor showed that the SpA leaching from the columns was present in polymerized or oligomerized form. HPLC analysis showed a broad peak indicative of several species of high molecular weight protein oligomers. The results indicate that SpA oligomers dissociated from sites of non-covalent binding on the SpA-silica column. These crosslinked molecular species appear to have been formed during the immobilization procedure as a result of carbodiimide crosslinking of free Staphylococcal SpA to itself forming higher molecular weight species that remained associated non-covalently with the silane-derivatized silica surface.

The infusion of these high molecular weight SpA polymers into patients may be a comprehensive explanation for the therapeutic effect of SpA immunoadsorbent columns in ITP and RA. The pathophysiology of ITP is known to involve the opsonization of antibody-sensitized platelets by macrophages in spleen and liver (Karpatin, S., *Semin. Hematol.* 22:260 (1985)). RA is thought to be mediated by FcR bearing macrophages. As described above, crosslinked oligomeric SpA forms complexes with IgG in plasma and, upon reinfusion, these large complexes, would block reticuloendothelial (primarily FcR) function as they bind to these receptors on lymphocytes and/or macrophages. Additionally or alternatively, such complexes would block destruction of antibody-sensitized platelets by splenic or liver macrophages. Free or convertible SpA may also bind to circulating antiplatelet antibodies inhibiting their opsonizing function. Hence, infused SpA polymers or SpA polymer-IgG complexes can exert their effect at the level of both effector (lymphocyte/macrophage) and target (sensitized platelet) cells. The net effect of these infused complexes would be further amplified when as many as six additional rounds of treatment using the Prosorba® column (as recommended by the IMRE Corporation) are employed. During this treatment period, several hundred micrograms of these complexes might be administered to patients.

On theoretical grounds alone, the polymeric SpA-IgG complexes are expected to be far more potent in binding and crosslinking FcRs than would be equimolar amounts of monomeric SpA-IgG complexes. This could lead to cell activation or inactivation, depending on the subtype of FcR, the cell type encountered and the conditions of binding to the receptor. Indeed protein-A IgG complexes in certain ratios may augment the incorporation into target cell (Shearer, W. T. el al., *J Immunol.* 132:2279–2284). For example, crosslinking of the FcRII of B lymphocytes by polymeric SpA-IgG complexes could generate signals which abort cell activation, proliferation and antibody secretion (Ravetch, J. V. *Cell* 78:553 (1994)). Alternatively, the SpA-superantigen-IgG polymer may promote cognate interaction of B cells with T cells via class II binding of the enterotoxins to B cells and TcR Vβ regions resulting in enhanced T cell regulatory responses and/or T cell anergy (Mourad, W. et al., *J. Exp. Med* 170:2011–2022 (1989); Fuleihan, R. et al., *J Immunol.* 146:1661–1666 (1991)). Antibody responses may be enhanced by targeting antigens to the FcγRI/CD64 receptor on monocytes and myeloid cells. See, for example, Gosselin, E. J. et al., *J Immunol.* 149:3477–3481 (1992) Heijnen, I. A. F. M. et al., *J Clin. Invest.* 97:331–338 (1996). Therefore, SpA-superantigen-IgG polymer may be used to regulate antigen presentation and the resultant antibody responses.

In summary, the SpA polymers and polymeric conjugates of the present invention represent a quantum advance in potency over the monomeric SpA. These polymers work in very small quantities and are able to block ADCC and rosette formation at μmolar concentrations, far lower than are monomeric SpA-IgG complexes. This accounts for their enormous potency when given in such small amounts. The present inventor believes that the FcR blocking effects of the polymerized SpA is a major mechanism for the observed effects, though they do not wish to be bound by this mechanism. Other mechanisms may well be operative.

Once the present invention had been conceived and reduced to practice, an explanation for the toxicity of Prosorba® column therapy became available based on the known biologic activities of these high molecular weight complexes and further by the presence (predicted and proven by the present inventor) of enterotoxin B (and other enterotoxins) in the column perfusate. IgG-SpA complexes in IgG excess (as would develop in the "off line" mode of Prosorba® therapy) can act like IgM complexes, and are clearly biologically active in sub μgram quantities especially in complement consumption and anaphylatoxin generation. This would account for the consistent reports of significant complement activation and anaphylatoxin generation in serum of patients after Prosorba® treatment (Langone, J. J. et al., *J Immunol.* 18:29 (1984); Sjoquist, J. et al., *J Immunol.* 103:467 (1989); Langone, J. J. et al., *J Immunol.* 121:327 (1978); Langone, J. J. et al., *Mol. Cell. Biochem.* 65:159 (1984)). IgG-SpA complexes also bind to FcRs of platelets leading to activation and release serotonin and other mediators (Hawiger et al., supra). Complex deposition in blood vessels in vivo, can initiate leukocytoclastic vasculitis while platelet activation could promote clotting and systemic embolus formation.

In conclusion, SpA oligomers or polymers can be manufactured under controlled chemical conditions and administered in appropriate doses in place of using the cumbersome, uncontrolled and almost inadvertent method of plasma perfusion over SpA-silica immunoadsorbent columns. The unpredictable, and often dangerous, therapeutic performance of the column can be eliminated with a reduction in toxicity and an enhancement in safety for human use.

An adjunct to the discoveries made by the present inventor is the observation that the displaceable SpA oligomers eluting from the SpA columns can be readily quantitated and monitored to facilitate standardization of the output of this material from the SpA immunoadsorbent columns already in clinical use. Monitoring SpA monomers and oligomers as well as enterotoxins in column perfusates will allow consistent administration of an effective therapeutic dose of SpA and a reduction in toxicity associated with the use of these columns.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A composition comprising a mixture of monomeric and crosslinked polymeric protein A molecules or a functional derivative of protein A molecules, wherein (a) said cross-linked polymer molecule comprises at least two monomeric units of protein A or of said functional derivative; and (b) at least 10% of the total protein A or functional derivative in the form of polymers.

2. A composition according to claim 1, wherein said polymers have a range of molecular masses from about 12 kDa to about 10,000 kDa.

3. A composition according to claim 1, wherein (a) the average molecular mass of the polymeric protein A molecules or functional derivative of a protein A molecules is at least about 500 kDa; and (b) at least about 50% of the total protein A or functional derivative is in the form of polymers.

4. A composition according to claim 1, wherein (a) the average molecular mass of the polymeric protein A molecules or functional derivative of protein A molecules is between about 64 kDa and about 1000 kDa; and (b) at least about 70% of the total protein A or functional derivative is in the form of polymers.

5. A composition according to claim 1, wherein (a) the average molecular mass of the polymeric protein A molecules or functional derivative of protein A molecules is between about 64 kDa and about 10,000 kDa; and (b) at least about 90% of the total protein A or functional derivative is in the form of polymers.

6. A composition according to claim 1, wherein said polymeric protein A or polymeric functional derivative molecules are complexed with immunoglobulin molecules to form polymeric protein A-immunoglobulin complexes.

7. A composition comprising a composition according to claim 6, wherein said complexes are further complexed with complement components that bind to the immunoglobulin molecules to form protein A-immunoglobulin-complement complexes.

8. A composition according to claim 6, wherein said immunoglobulin is IgG.

9. A composition according to claim 8, wherein said IgG is a purified specific antibody.

10. A composition according to claim 9 wherein said antibody is a monoclonal antibody.

11. A composition according to claim 1, wherein said protein A is further crosslinked with molecules of a bacterial superantigen or a functional derivative thereof to form a mixture comprising (a) polymeric crosslinked protein A or protein A functional derivative, (b) polymeric crosslinked conjugates selected from the group consisting of i. protein A-superantigen, ii. protein A functional derivative-superantigen, iii. protein A-superantigen functional derivative, and iv. protein A functional derivative-superantigen functional derivative; and (c) polymeric crosslinked superantigen or superantigen functional derivative.

12. A composition according to claim 11, wherein said bacterial superantigen is selected from a group consisting of an enterotoxin of *Staphylococcus aureus*, toxic shock syndrome toxin, a *Streptococcus pyrogenic* exotoxin, a *Mycoplasma arthritides* toxin and a *Yersinia enterocolitica* toxin.

13. A composition comprising a chemically crosslinked polymer of protein A, or for a functional derivative of protein A, and having the following characteristics:

(a) immunoglobulin Fc binding activity is less than half that of protein A; and (b) immunoglobulin $V_H3$ region binding is more than about twice that of native protein A.

14. A composition according to claim 13, wherein said protein A polymer is further crosslinked to molecules of a bacterial superantigen or to a superantigen functional derivative.

15. A method for preparing a composition according to claim 1, comprising treating protein A or said functional derivative with a crosslinking agent under conditions which result in crosslinking of said protein A or said functional derivative or both to produce said composition, and recovering said composition.

16. A method for preparing a composition according to claim 11, comprising treating a mixture of Protein A or its functional derivative and a bacterial superantigen or its functional derivative with a crosslinking agent under conditions which result in crosslinking of any one or more of:

(a) protein. A or i its functional derivative with like molecules;

(b) protein A with superantigen;

(c) protein A functional derivative with superantigen;

(d) protein A with superantigen functional derivative;

(e) protein A functional derivative with superantigen functional derivative (f) superantigen or its functional derivative with like molecules, and recovering said composition.

17. A method according to claim 15, wherein said crosslinking agent is selected from the group consisting of a carbodiimide, a homobifunctional aldehyde, a homobifunctional epoxide, homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional razide, a homobifunctional diazonium derivative and a homobifunctional photoreactive compound.

18. A method according to claim 15, wherein said crosslinking agent is a heterobifunctional compound selected from the group consisting of compounds having:

(a) an amine-reactive and a sulfhydryl-reactive group;

(b) an amine-reactive and a photoreactive group; and (c) a carbonyl-reactive and a sulfhydryl-reactive group.

19. A method according to claim 15, wherein said crosslinking is performed by coupling a carbonyl group to an amine group or to a hydrazide group by reductive amination.

20. A method according to claim 17 wherein said crosslinking agent is a carbodiimide selected from the group consisting of 1-cyclohexyl-3-(2-morpholinyl-(4-ethyl) carbodiimide, 1 - ethyl - 3 - ( 3 -dimethyaminopropyl) carbodiimide and 1-ethyl-3- (4-azonia-4,4-dimethylpentyl) carbodiimide.

21. A method according to claim 20, wherein said carbodiimide is 1-cyclohexyl-3-(2-morpholinyl-(4-ethyl) carbodiimide.

22. A method for preparing a composition according to claim 11, comprising crosslinking said mixture of protein A or its functional derivative and said superantigen or its functional derivative with a carrier which carrier consists of a protein, lipid or other polymer which can be covalently bonded to said protein A or said derivative and said superantigen, thereby creating a heterogenous polymer complex, and recovering said heterogenous polymer complex.

23. A method according to claim 22, wherein said carrier is a protein selected from the group consisting of serum albumin, keyhole limpet hemocyanin, tetanus toxoid, ovalbumin, thyroglobulin, diphtheria toxoid, myoglobin, immunoglobulin and purified protein derivative of tuberculin.

24. A method according to claim 22, wherein said carrier is a polymer selected from the group consisting of a polysaccharide, a poly(amino acid), a poly(vinylalcohol), a polyvinylpyrrolidone, a poly(acrylic acid), a polyurethane and a polyphosphazene.

25. A method according to claim 22, wherein said crosslinking produces a polymer or polymer conjugate covalently bonded to a liposome.

26. A method according to claim 16, wherein said bacterial superantigen is selected from a group consisting of an enterotoxin of *Staphylococcus aureus*, toxic shock syndrome toxin, a *Streptococcus pyrogenic* exotoxin, a *Mycoplasma arthritides* toxin and a *Yersinia enterocolitica* toxin.

27. A pharmaceutical composition useful for treating a subject with an autoimmune or neoplastic disease, comprising (a) an effective amount of a composition according to any of claim 1–14; and (b) a pharmaceutically acceptable excipient or carrier.

28. A pharmaceutical composition useful for treating a subject with an autoimmune or neoplastic disease, comprising (a) an effective amount of a composition according to claim 1; and (b) a pharmaceutically acceptable excipient or carrier wherein said composition is further bonded to or sequestered within a liposome vesicle.

29. A method of treating a subject with an autoimmune disease or cancer, comprising administering to said subject a pharmaceutical composition according to claim 27.

* * * * *